US007022843B1

(12) United States Patent
MacAlpine et al.

(10) Patent No.: US 7,022,843 B1
(45) Date of Patent: *Apr. 4, 2006

(54) β,β'-DIHYDROXY MESO-SUBSTITUTED CHLORINS, ISOBACTERIOCHLORINS, AND BACTERIOCHLORINS

(75) Inventors: Jill Kirsten MacAlpine, Alexandria, VA (US); Christian Brückner, Storrs, CT (US); David Dolphin, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/551,159

(22) Filed: Apr. 14, 2000

Related U.S. Application Data

(60) Provisional application No. 60/129,324, filed on Apr. 14, 1999.

(51) Int. Cl.
*C07D 487/22* (2006.01)
(52) U.S. Cl. .................. 540/474; 540/145; 540/472
(58) Field of Classification Search ............... 514/410, 514/912; 540/145, 472, 475, 474, 912
See application file for complete search history.

(56) References Cited

U.S. PATENT DOCUMENTS

| 4,512,762 A | 4/1985 | Spears ..................... 604/21 |
| 4,932,934 A | 6/1990 | Dougherty ................ 604/21 |
| 5,283,255 A | 2/1994 | Levy et al. ................ 514/410 |
| 5,360,734 A | 11/1994 | Chapman et al. .......... 435/238 |
| 5,648,485 A | 7/1997 | Dolphin et al. ............ 540/474 |
| 5,756,541 A | 5/1998 | Strong et al. ............. 514/502 |
| 5,776,966 A | 7/1998 | North ...................... 514/410 |
| 5,798,349 A | 8/1998 | Levy et al. ................ 514/185 |
| 5,807,881 A | 9/1998 | Leong et al. .............. 514/410 |
| 5,834,503 A | 11/1998 | Kelly et al. ............... 514/410 |
| 5,868,695 A | 2/1999 | Wolf, Jr. et al. ............. 604/4 |
| 5,882,328 A | 3/1999 | Levy et al. ................ 604/20 |
| 6,043,237 A | 3/2000 | Meadows et al. .......... 514/185 |

FOREIGN PATENT DOCUMENTS

WO   WO 96/13504   5/1996

OTHER PUBLICATIONS

Berenbaum, M.C. et al. (1986). "Meso-Tetra(Hydroxyphenyl)Porphyrines, a New Class of Potent Tumour Photosensitisers with Favourable Selectivity," *Br J Cancer* 54:717-725.
Bonnett, R. In: "*Photosensitizing Compounds: their Chemistry, Biology and Clinical Use,*" Wiley, Chichester, Ciba Foundation Symposium 1989, 146, pp. 40-59, 79.
Bonnett, R. et al. (1991). "Photodynamic Therapy with Chlorins for Diffuse Malignant Mesothelioma: Initial Clinical Results," *Br. J. Cancer* 64:1116-1120.

Bonnett, R. (1993). "New Photosensitisers for the Photodynamic Therapy of Tumours," *SPIE* 2078:74-90.
Bonnett, R. (1995). "Studies on 5,10,15,20-Tetrakis(m-hydroxyphenyl)chlorin, m-THPC (TEMOPORFIN)," *Proc SPIE* 2371:31-38.
Bruckner, C. et al. (1995). "2,3-*vic*-Dihydroxy-*meso*-tetraphenylchlorins from the Osmium Tetroxide Oxidation of *meso*-Tetraphenylporphyrin," *Tetrahedron Lett* 36:3295-3298.
Bruckner, C. et al. (1995). "β,β'-Dixydroxylation of *meso*-Tetraphenylchlorins and Metallochlorins," *Tetrahedron Lett* 36:9425-9428.
Fisher, A.M.R. et al. (1995). "Clinical and Preclinical Photodynamic Therapy," *Lasers in Surgery and Medicine* 17:2-31.
Hassan, M.G.A. et al. (1977). "N-Methylated Tetraphenylporphyrines," *J Chem Soc.,* Perkin 1:98-103.
Kessel, D. (1986). "Porphyrin-Lipoprotein Association as a Factor in Porphyrin Localization," *Cancer Lett* 33:183-188.
Kongshaug, M. (1992). "Distribution of Tetrapyrrole Photosensitizers Among Human Plasma Proteins," *Int J Biochem* 24:12391265.
Khosopour, R. et al. (1972). "A General Mechanism for Metal Ion Incorporation into Porphyrin Molecules," *J Chem Soc., Chem Comm* 13-14.
Mossman, T. (1983). "Rapid Colorimetric Assay for Cellular Growth and Survival: Application to Proliferation and Cytotoxic Assays," *J Immunol Meth* 65:55-63.
Ochsner, M.et al. (1997). "Photodynamic Therapy: The Clinical Perspective," *Drug Res* 47(11):1185-1194.
Redmond, R.W . et al. "Aggregation Effects on the Photophysical Properties of Porphyrines in Relation to Mechanisms Involved in Photodynamic Therapy," *Methods in Porphyrin Photosensitization* v.193, Kessel, D. Ed.; Plenum, New York, 1985, 293-302.
Richter,A.M. et al. (1990). "In Vitro Evaluation of Phototoxic Properties of Four Structurally Relatred Benzoporphyrin Derivatives," *Photochem Photobiol:* 52(3): 495-500.
Spikes, J.D. "The Role of the Anatomy, Physiology and Biochemistry of Tumors in the Selective Retention of Sensitizers and the mechanisms of Photosensitized Tumor Destruction," In: "*Light in Biology and Medicine,*" v.1. Douglas, R.A. et al.Eds.; Plenum, New York, 1988, p. 105-113.

(Continued)

Primary Examiner—Zohreh Fay
(74) Attorney, Agent, or Firm—Morrison & Foerster LLP

(57) ABSTRACT

Improved β,β'-dihydroxy meso-substituted chlorin, bacteriochlorin or isobacteriochlorin compounds are provided as photosensitizers. Pharmaceutical compositions and photodynamic therapy comprising them are also disclosed.

7 Claims, 9 Drawing Sheets

OTHER PUBLICATIONS

Spilleer, W. (1998). "Singlet Oxygen Quatum Yields of Different Photosensitizers in Polar Solvents and Micellar Solutions," *J. Porphyrines and Phthalocyanines* 2:145-158.

Van Lier.(1991). "Phot0sensitization: Reaction Pathways," Photobiological Techniques 216:85-98.

Faustino, M.F.A. et al. *Tetrahedron Lett,* NL Elsevier Science Publishers, Amsterdam (1996) 37(20):3569-3570.

Sisemore M.F. et al. *Inorg Chem* (1997) 36:979-984.

(125)

β,β'-DIHYDROXY MESO-SUBSTITUTED CHLORINS, ISOBACTERIOCHLORINS, AND BACTERIOCHLORINS

RELATED APPLICATIONS

This application claims benefit of priority from U.S. Provisional Application 60/129,324, filed Apr. 14, 1999, which is hereby incorporated by reference as if fully set forth.

FIELD OF THE INVENTION

The present invention relates to certain improved dihydroxy chlorin, bacteriochlorin or isobacteriochlorin compounds and their preparation for use in photodynamic therapy (PDT). In particular, the invention relates to analogs of dihydroxylated β,β'-unsubstituted tetrapyrrolic macrocycles that have increased toxicities. Many of these compounds are useful photosensitizers in PDT for mediating the destruction of unwanted cells or tissues or other undesirable materials by irradiation.

BACKGROUND ART

Photodynamic therapy (PDT) generally involves the administration of compounds that are capable of absorbing light, typically in the visible range, but also in the near ultraviolet, followed by irradiation of locations in the subject for which a toxic, inhibitory or modulatory effect is desired. PDT was initially developed using hematoporphyrin and related compounds in the treatment of tumors, as it appeared that these compounds would "home" to locations containing rapidly dividing cells. The tumor could then be irradiated with light absorbed by the hematoporphyrin and destruction of the surrounding tissue resulted (for example, see U.S. Pat. Nos. 4,932,934 and 5,283,255). PDT has since been shown to be useful for treatment of my other conditions, including ocular diseases characterized by unwanted neovascularization, such as aged-related macular degeneration (see U.S. Pat. Nos. 5,756,541 and 5,798,349), the inhibition of secondary cataract formation in the eye (U.S. Pat. No. 6,043,237), the impairment of blood-borne targets such as leukemic cells and immunoreactive cells (U.S. Pat. Nos., 5,776,966, 5,807,881 and 5,868,695) the removal of unwanted microorganisms (U.S. Pat. No. 5,360,734), the removal of atherosclerotic plaque (U.S. Pat. No. 5,834,503) as well as the prevention of transplant rejection by pre-treating the graft tissue (U.S. Pat. No. 5,882,328).

The search for effective photosensitizers requires a two-pronged approach. The optimization of photophysical properties is key to any promising drug as the compounds must absorb at long wavelengths. The development of higher wavelength photosensitizers requires a synthetic method which can generate a number of analogs with ease because in vivo biological proficiency is known to increase on going from porphyrins to chlorins to bacteriochlorins. Compounds must also display good biodistribution properties in order to be effective. The correlation between the biodistribution of photosensitizers and the structure of the drug is complex. This complexity is increased with hydrophobic molecules which must be formulated into a suitable transport system such as liposomes, emulsions or nanoparticles. The delivery systems of these drugs are crucial and have been a key obstacle in PDT. These systems are complicated in that their nature drastically affects both the rate and the amount of drug taken up by the cells.

A very large percentage of porphyrin-based photosensitizers are transported via protein binding. For example, at least 95% of hematoporphyrin (Hp) at the normal dose used for PDT (3–5 mg/kg body weight) is complexed by serum proteins (Jori, G. in Photosensitizing Compounds: their Chemistry, Biology and Clinical Use. Wiley, Chichester. Ciba Foundation Symposium 1989, 146, 79). Human serum consists of three protein fractions: lipoproteins (high density (HDL), low density (LDL) and very low density (VLDL)), globulins and albumin. The distribution of photosensitizers in the serum is strongly dependent upon their chemical structure. Hydrophilic, polar photosensitizers are bound preferentially by albumin and globulins whilst hydrophobic molecules are bound by lipoproteins (Ochsner, M. Arzneim.-Forsch./Drug Res. 1997, 47(II), 1185–1194).

Albumin and globulins are known to possess a distinct number of binding sites (Kessel, D. Cancer Lett. 1986, 33, 183). The binding of photosensitizer molecules to albumin and globulin is governed by a chemical equilibrium between the bound and unbound photosensitizer (Supra). In contrast, the binding of hydrophobic dyes to lipoproteins reflects a partition of the photosensitizer between the lipid and the aqueous phase and therefore many photosensitizer molecules can bind to each lipoprotein. The relative binding of tetrapyrroles to lipoproteins has been shown to increase with decreasing polarity (Bonnett, R. SPIE 1993, 2078, 74). The partitioning of hydrophobic photosensitizers is significant as these dyes tend to aggregate in aqueous systems. The extent of aggregation is dependent upon the polarity of the substituents on the porphyrin skeleton (Redmond, R. W.; Land, E. J.; Truscott, T. G. in Advances in Experimental Medicine and Biology. Volume 193. Kessel, D. Ed.; Plenum, N.Y., 1985, 293). Only monomeric nonaggregated molecules are photoactive and therefore any aggregation will decrease the observed cytotoxicity of the drug (Ibid, p. 301).

Hydrophobic photosensitizers must, therefore, be properly formulated in order to counteract their natural tendency to aggregate in aqueous systems. An advantage of hydrophobic drugs is their preferential binding to lipoproteins as tumor cells express a much larger number of receptors for low density lipoproteins (LDL) than do most normal cells (Spikes, J. D. in Light in Biology and Medicine Vol. 1. Douglas, R. A.; Moan, J.; Dall'Acqua F. Eds.; Plenum, N.Y., 1988, p. 105). These receptors specifically recognize LDL and promote their internalization by cells via the formation of coated pits. Photosensitizers that bind to LDL are endocytosed by the neoplastic cells along with the lipoprotein (Fisher, A. M. R.; Murphree, A. L.; Gomer, C. J. Lasers in Surgery and Medicine 1993, 17, 2). Once inside the cell, the photosensitizer is released into the cytoplasm and binds to apolar endocellular matrices such as mitochondria, lysosomes and plasma membranes. A photosensitizer will be most effective if it displays an affinity for tumor cells versus normal cells because low cytotoxicity of such a drug can be overcome by increasing the dose. In the early 1980s, ortho-, meta- and para-isomers of meso-tetra(hydroxyphenyl)porphyrin were investigated for use as photosensitizers (Berenbaum, M. C.; Akande, S. L.; Bonnett, R.; Kaur, H.; Ioannou, S.; White, R. D.; Winfield, U.-J. Br. J. Cancer 1986, 54, 717). In order to increase the absorption in the red region, the analogous chlorins and the meta-hydroxy substituted bacteriochlorin were synthesized (Bonnett, R.; Berenbaum, M. in Photosensitizing Compounds: their Chemistry, Biology and Clinical Use. Wiley, Chichester. Ciba Foundation Symposium 1989, 146, 40–59). In vivo testing showed that both phototoxicity (reflected by the decreased dose) and tissue penetration (reflected by the increased depth of necrosis) increased as did the level of reduction of the porphyrin (Bonnett, R. Proc. SPIE 1995, 2371, 31). Tetra (m-hydroxyphenyl)chlorin was chosen as the most suitable for clinical trials and was found to be 25–30 times more effective than HpD in destroying tumors as observed by in vivo bioassays with LD50=3 mg/kg (Bonnett, R.; Berenbaum, M. Br. J. Cancer 1991, 64, 1116). Tetra(m-hydroxyphenyl)chlorin showed 90% tumor necrosis with only 10% recurrence, but side effects such as extended skin sensitivity, severe chest pains and loss of appetite were also observed.

The β,β'-dihydroxylation of meso-tetraphenylporphyrins and mesotetraphenyl chlorins via osmium tetroxide mediated oxidation has been previously described and patented (Bruckner, C.; Dolphin, D. Tetrahedron Lett. 1995, 36, 9425; and Bruckner, C.; Dolphin, D. Tetrahedron Lett. 1995, 36, 3295) and U.S. Pat. No. 5,648,485 issued Nov. 3, 1998, which is hereby incorporated by reference as if fully set forth.

DISCLOSURE OF THE INVENTION

The invention relates to the synthesis of a number of variously substituted monophenyl, diphenyl, triphenyl, and tetraphenyl-porphyrins and the subsequent formation of the analogous dihydroxy chlorins via the osmium tetroxide oxidation reaction. Preferred are compounds substituted at the meta (m) position which are more cytotoxic than the analogous compounds substituted at the para (p) position. Without being bound by theory, this may be attributed to the self-aggregation of para-substituted compounds which is hindered by the presence of substituents in the meta position. It is possible that hydrophobicity, aggregation and amphiphilicity affect the observed cytotoxicity of the compounds of the invention.

Thus according to the present invention, there have been prepared novel β,β'-dihydroxy meso-substituted chlorin, isobacteriochlorin and bacteriochlorin compounds having the formula (I) or (II):

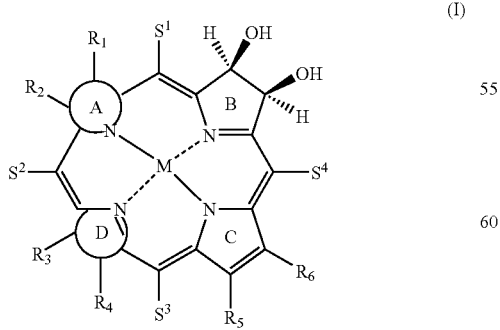

(I)

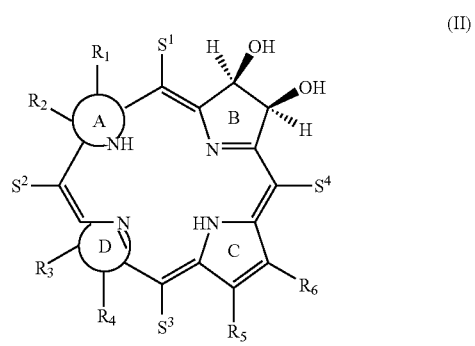

(II)

wherein M is a metal selected from the group consisting of Ni(II), Cu(II), Zn(II),
Fe(III)Cl, Sn, Ge, Si, Ga, Al, Mn(III), Gd(III), In and Tc;
A is a ring having the structure:

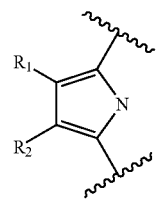

or

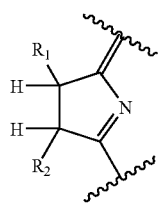

or

D is a ring having the structure:

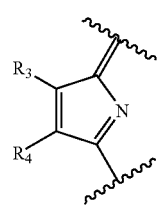

or

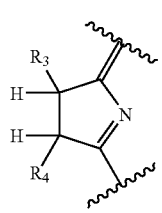

or or

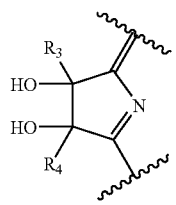

R₁ through R₆ are independently a hydrogen atom, a lower alkyl group, a lower alkyl carboxylic acid or acid ester group, keto, hydroxy, nitro, amino or a group that, taken together with another ring, ring substituent or meso-substituent, forms a fused 5- or 6-membered ring; and at least $S^2$ or $S^4$ is a phenyl group while $S^1$ and $S^3$ are independently selected from H, substituted or unsubstituted alkyl groups, or substituted or unsubstituted aromatic rings, which may be the same or different.

In a particularly preferred aspect of the invention, a dihydroxy diphenylchlorin, diphenyl-2,3-dihydroxychlorin, was synthesized and tested for potential as photosensitizers for photodynamic therapy. This compound was found to be surprisingly potent as a photosensitizer, with an LD50 value of 1.2 ng/mL. This compound is, therefore, 450 times more potent than the commercially available photosensitizer Photofrin™. The compound was synthesized by oxidation of diphenylporphyrin with osmiumtetroxide in the same manner as with tetraphenylporphyrins with the exception that the reaction only required 3 hours, possibly due to the lack of steric hindrance as compared to the tetraphenylporphyrin reaction. The compound bears no substituents on the phenyl rings and any substituents on these phenyl would affect its cytotoxicity. Thus the present invention is directed to encompass additional analogs of diphenyl-2,3-dihydroxychlorin containing substituents at other positions.

In another aspect of the invention, the osmium tetroxide reaction was improved by decreasing the reaction time to allow increased catalysis. The compound N-methyl TPP (compound 31), known to be distorted from planarity and activated towards certain reactions, was used as a starting material in the reaction. The osmium tetroxide oxidation of N-methyl TPP was successful as the reaction required only 6–12 hours for completion.

BRIEF DESCRIPTION OF DRAWINGS

The present invention will be more clearly understood by referring to the following drawings, in which.

MODES OF CARRYING OUT THE INVENTION

Figure 1:
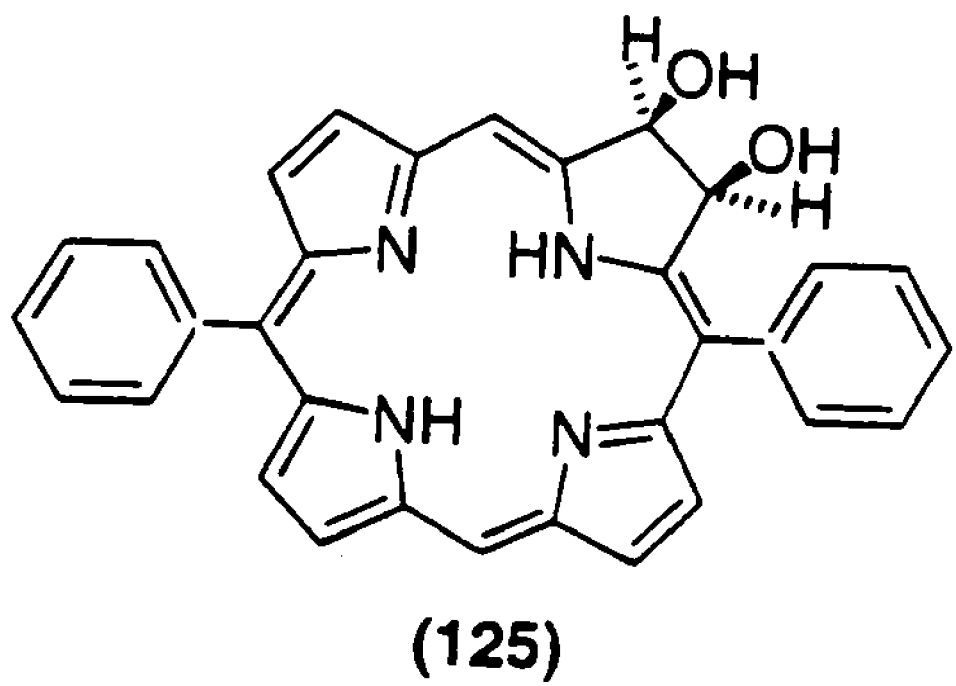
FIG. 1 shows the structure of diphenyl-2,3-dihydroxychlorin.
Figure 2:
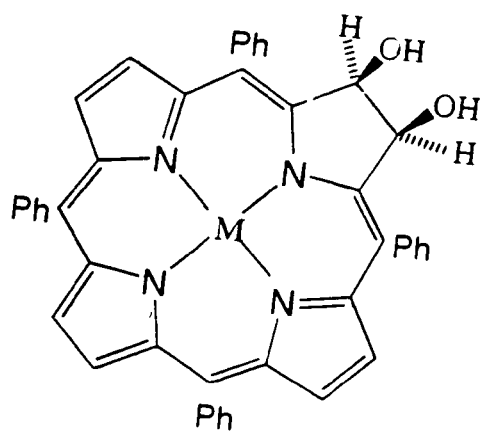
FIG. 2 shows the UV-Vis spectra of the diols are typical for chlorins with λmax (log ε) 408 (5.27), 518 (4.19), 548 (4.19), 592 (3.85), 644 (4.38) nm in methylene chloride. Typical chlorin ¹H-NMR spectra were obtained for the diol chlorins.
Figure 2:
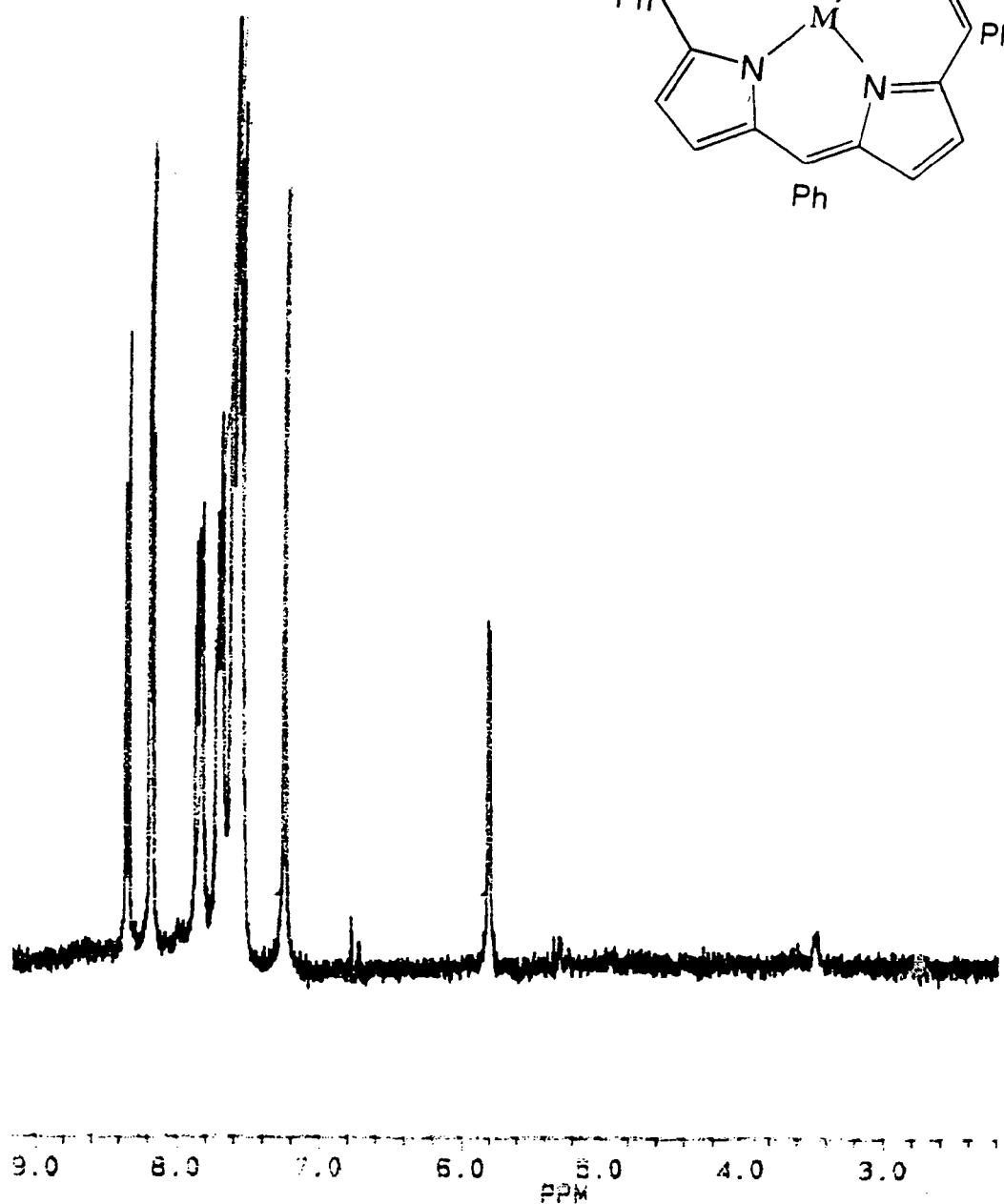

The β,β'-dihydroxy meso-substituted chlorin, bacteriochlorin or isobacteriochlorin compounds of the invention have formula (I) or formula (II), as described and shown above. M in formula (I) can be any metal species that is capable of forming the complex of formula (I), but is preferably selected from the group consisting of Ni(II), Cu(II), Zn, Sn, Ge, Si, Ga and Al. An important characteristic of the metal selected is that it should be possible to introduce the metal into the porphyrin structure and then also possible to remove it from the chlorin resulting from the process of the invention.

A can be any ring having the structure:

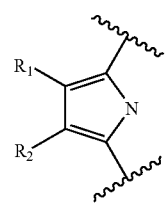

or

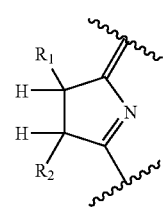

or

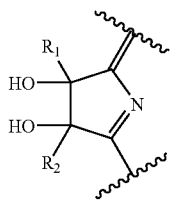

D can be any ring having the structure:

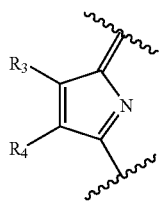

or

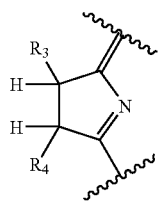

or

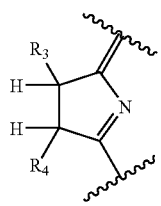

It should be understood that all corresponding resonance forms of the above structures are also intended to be covered by the terms "A" and "D". Preferably, however, at least one of the rings A and D is identical to the rings B and C. Even more preferably, both rings A and D are identical to the other rings B and C and, with them, form a porphyrin core structure having four such rings, each ring being connected by a bridging carbon atom that is referred to as the meso-position.

$R_1$ through $R_6$ can be any one of a large number of ring substituents, so long as they do not interfere with the osmylation and reduction steps outlined above. Preferably, $R_1$ through $R_6$ are independently a hydrogen atom; a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl; a carboxylic acid ester group, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_2CH_3$, —$CH_2CH(CH_3)_2COOCH_2CH_3$; keto; hydroxy; nitro; amino; or the like.

Further, $R_1$ and $R_2$, $R_3$ and $R_4$, or $R_5$ and $R_6$, can be taken together with another ring, ring substituent or meso-substituent to form a fused 5- or 6-membered ring. The fused 5- or 6-membered ring so formed may be any saturated or unsaturated, carbocyclic or heterocyclic 5- or 6-membered ring that does not interfere with the osmylation and reduction reaction steps of the invention. Examples of such rings include cyclopentane, furan, thiophene, pyrrole, isopyrrole, 3-isopyrrole pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiathiazole, 1,2,4-oxadiazole, 1,2,5-oxadiazole, 1,3,4-oxadiazole, 1,2,3-dioxazole, 1,2,4-dioxazole, 1,2,5-oxathiazole, 1,3-oxathiole, benzene, cyclohexane, 1,2-pyran, 1,4-pyran, 1,2-pyrone, 1,4-pyrone, 1,2-dioxin, 1,3-dioxin (dihydro form), pyridine, pyridazine, pyrimidine, pyrazine, piperazine, 1,3,5-triazine, 1,2,4-triazine, 1,2,4-oxazine, 1,3,2-oxazine, o-isoxazine, 1,2,5-oxathiazine, 1,4-oxazine, p-isoxazine, 1,2,6-oxathiazine, 1,3,5,2-oxadiazine, morpholine, azepine, oxepin, thiepin, 1,2,4-diazepine, and the like. Preferably, when $R_1$ and $R_2$, $R_3$ and $R_4$, or $R_5$ and $R_6$, form a fused, 5- to 6-membered ring, the ring is a 6-membered ring. Most preferably, when $R_1$ and $R_2$, $R_3$ and $R_4$, or $R_5$ and $R_6$, form a ring, it is a 6-membered carbocyclic ring, i.e., a benzene ring.

In a particularly preferred embodiment, $R_1$ through $R_6$ are independently hydrogen, methyl, ethyl, or lower alkyl esters, most preferably being hydrogen, methyl or ethyl.

Preferably, at least one of $S^1$ to $S^4$ is a phenyl group and the remaining S positions are independently selected from H, any one of a large number of substituted or unsubstituted alkyl groups, substituted or unsubstituted cycloalkyl groups, and aromatic rings. When one or more of $S^1$ through $S^4$ is an alkyl group, they preferably have from about 1 to about 18 carbon atoms, more preferably about 1 to 12 carbon atoms and, even more preferably, about 1–6 carbon atoms. Examples of typical alkyl groups are methyl, ethyl, isopropyl, sec-butyl, tert-butyl, n-pentyl and n-octyl.

When one or more of $S^1$ through $S^4$ is an alkyl group, it may be unsubstituted or substituted with any group that does not interfere with the osmylation or reduction reactions. For example, when one or more of $S^1$ through $S^4$ is an alkyl group may be substituted by a halogen atom, such as fluorine, chlorine or bromine; a hydroxy group, such as in pentoses and hexoses; thiol; or a carbonyl group, such as when the alkyl group is an aldehyde, ketone, carboxylic acid (e.g., a fatty acid) or ester or amide; a primary, secondary, tertiary, or quaternary amino group; nitrile; a phosphate group; a sulfonate group; and the like.

When one or more of $S^1$ through $S^4$ is a cycloalkyl group, it preferably contains from about 3 to about 7 carbon atoms. Examples of typical cycloalkyl groups include cyclopropyl, cyclohexyl, and cycloheteroalkyl, such as glucopyranose or fructofuranose sugars. When one or more of $S^1$ through $S^4$ is a cycloalkyl group, it may be unsubstituted or substituted with any group that does not interfere with the osmylation or reduction reactions. For example, when one or more of $S^1$ through $S^4$ is a cycloalkyl group, they may be substituted by any of the same substituents described above for the case when one or more of $S^1$ through $S^4$ is an alkyl group.

When one or more of $S^1$ through $S^4$ is an aryl group, it preferably contains from about 5 to about 12 carbon atoms, optionally containing one or more heteroatoms, and optionally including rings that are fused to the existing conjugated porphyrin ring structure. Examples of suitable aromatic rings include furan, thiophene, pyrrole, isopyrrole, 3-isopyrrole, pyrazole, 2-isoimidazole, 1,2,3-triazole, 1,2,4-triazole, 1,2-dithiole, 1,3-dithiole, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxathiazole, 1,3-oxathiole, benzene, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazone, 1,2,4-triazine, 1,2,3-triazine, 1,2,4-oxazine, 1,3,2-oxazine, 1,3,6-oxazine, 1,4-oxazine, o-isoxazine, p-isoxazine, 1,2,5-oxathiazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, naphthalene, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodianzine, naphthyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, anthracene, phenanthrene, carbazole, xanthene, acridine, purine, steroidal compounds and the like.

In a particularly preferred embodiment, both $S^2$ and $S^4$ are phenyl groups.

In another embodiment, at least one of $S^1$ through $S^4$ has the structure:

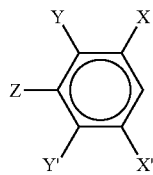

or

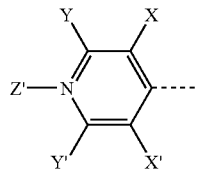

substituents and are generally used to "fine tune" the biological activity, the biodistribution, the absorption and clearance characteristics, and the physical properties of the desired product. One way in which this may be done by selecting substituents in such a manner that the compound of formula (I) or (II) is an amphiphilic molecule. By "amphiphilic" is meant the molecule becomes more asymmetric, such as (1) having both (a) a highly polar, water-soluble region and (b) a highly hydrophobic, water-insoluble region; or (2) having both (a) a nonionic region and (b) an ionic region.

However, it should be noted that the invention also includes β,β'-dihydroxy meso-substituted chlorin, bacteriochlorin or isobacteriochlorin compounds having substantially or exactly identical aryl substituents. Further, any aryl substituent chosen should also have no adverse effect on the ability of the compound to undergo the step "a." and step "b." reactions used to prepare the compounds of the invention.

Preferably, X, X', Y, Y' and Z are independently (1) hydrogen; (2) halogen, such as fluoro, chloro, iodo and bromo; (3) lower alkyl, such as methyl, ethyl, n-propyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salt, such as —$CH_2COOH$, —$CH_2COO-Na^+$, —$CH_2CH(Br)COOH$, —$CH_2CH(CH_3)COOH$, —$CH(Cl)$—$CH_2$—$CH(CH_3)$—$COOH$, —$CH_2$—$CH_2$—$C(CH_3)_2$—$COOH$, —$CH_2$—$CH_2$—$C(CH_3)_2$—$COO-K^+$, —$CH_2$—$CH_2$—$CH_2$—$CH_2$—$COOH$, $C(CH_3)_3$—$COOH$, $CH(Cl)_2$—$COOH$ and the like; (7) carboxylic acid ester, such as —$CH_2CH_2COOCH_3$, —$CH_2CH_2COOCH_2CH_3$, —$CH_2CH(CH_3)COOCH_2CH_3$, —$CH_2CH_2CH_2COOCH_2CH_2CH_3$, —$CH_2CH(CH_3)_2COOCH_2CH_3$, and the like; (8) sulfonic acid or acid salt, for example, group I and group II salts, ammonium salts, and organic cation salts such as alkyl and quaternary ammonium salts; (9) sulfonic acid ester, such as methyl sulfonate, ethyl sulfonate, cyclohexyl sulfonate and the like; (10) amino, such as unsubstituted primary amino, methylamino, ethylamino, n-propylamino, isopropylamino, 5-butylamino, sec-butylamino, dimethylamino, trimethylamino, diethylamino, triethylamino, di-n-propylamino, methylethylamino, dimethyl-sec-butylamino, 2-aminoethanoxy, ethylenediamino, 2-(N-methylamino) heptyl, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (11) cyano; (12) nitro; (13) a biologically active group; or (14) any other substituent that increases the amphiphilic nature of the compound of formula (I) or (II).

The term "biologically active group" can be any group that selectively promotes the accumulation, elimination, binding rate, or tightness of binding in a particular biological environment. For example, one category of biologically active groups is the substituents derived from sugars, specifically, (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-1-glucose; (6) O-methyl derivatives such as methyl I-glucoside, methyl J-glucoside, methyl I-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, L-gluconolactone, L-glucuronolactone, ascorbic acid, and dehydroascorbic acid; (10) phosphoric acid esters such as I-glucose 1-phosphoric acid, I-glucose 6-phosphoric acid, I-fructose 1,6-diphosphoric acid, and I-fructose 6-phosphoric acid; (11) deoxy sugars such as 2-deoxy-ribose, rhamnose (deoxymannose), and fucose (6-deoxy-galactose); (12) amino sugars such as glucosamine and galactosamine; muramic acid and neuraminic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as I-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; and (4) neurotransmitters, such as acetylcholine, serotonin, dopamine, and the like. Any analog of these substances that also succeeds in binding to a biological receptor is also included.

Particularly useful examples of substituents tending to increase the amphiphilic nature of the compound of formula (I) include: (1) long chain alcohols, for example, —$C_{12}H_{24}$—OH where —$C_{12}H_{24}$ is hydrophobic; (2) fatty acids and their salts, such as the sodium salt of the long-chain fatty acid oleic acid; (3) phosphoglycerides, such as phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidal choline; (4) sphingolipids, such as sphingomyelin; and (5) 17 glycolipids, such as glycosyldiacylglycerols, cerebrosides, sulfate esters of cerebrosides or gangliosides.

In a preferred embodiment, X, X', Y, Y' and Z are independently hydrogen, halogen, lower alkyl, lower alkoxy, hydroxy, carboxylic acid or acid salt, carboxylic acid ester, sulfonic acid or acid salt, sulfonic acid ester, substituted or unsubstituted amino, cyano, nitro, or a biologically active group, and Z' is hydrogen or lower alkyl. In another embodiment, X, Y, X' and Y' are each hydrogen, and Z is selected from the group consisting of hydrogen, halogen, lower alkyl, lower alkoxy, hydroxy, carboxylic acid, carboxylic acid ester, sulfonic acid ester (especially aromatic sulfonic acid ester), nitro, amino (especially lower alkyl amino), cyano, and a biologically active group.

In yet another embodiment, X, Y, Z, X' and Y' are selected from the group consisting of hydrogen, methyl, ethyl, t-butyl, methoxy, hydroxy, OR where R is an alkyl group or a fatty acid group having from 6 to 18 carbon atoms, fluoro, chloro, iodo, bromo, —C(O)—$OCH_3$, cyano, nitro, or a ligand specific for a biological receptor. In a further preferred embodiment, X, X', Y and Y' and Z is selected from the group consisting of hydrogen, halogen, lower alkyl, lower alkoxy, hydroxy, carboxylic acid or acid salt, carboxylic acid ester, sulfonic acid ester, sulfonic acid or acid salt, nitro, amino, cyano, and a biologically active group. In still another preferred embodiment, at least one of X, Y, Z, X' and Y' is a biologically active group or a substituent that increases the amphiphilic nature of the molecule.

Particularly preferred specific examples of groups that can serve as one or more of $S^1$ through $S^4$ include the following:

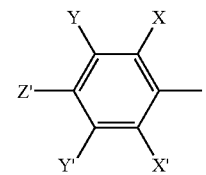

| X | X' | Y | Y' | Z |
|---|---|---|---|---|
| —H | —H | —H | —H | —H |
| —OH | —H | —H | —H | —H |
| —H | —H | —OH | —H | —H |
| —H | —H | —H | —H | —OH |
| —H | —H | —OH | —OH | —OH |
| —H | —H | —H | —H | —$SO_3$H(Na) |
| —$CH_3$ | —$CH_3$ | —H | —H | —CN |
| —H | —H | —$OCH_3$ | —$OCH_3$ | —$OCH_3$ |
| —H | —H | —H | —H | —COOH(Na) |
| —H | —H | —COOH(Na) | —COOH(Na) | —H |
| —H | —H | —H | —H | —$C_6H_{12}$COOH(Na) |
| —H | —H | —H | —$C_6H_{12}$COOH(Na) | —H |
| —H | —H | —$C_6H_{13}$ | —H | —$SO_3$H(Na) |
| —H | —H | —H | —COOH(Na) | -tert-Butyl |
| —H | —$CH_2NH_2$ | —H | —H | —H |
| —H | —H | —H | —H | —$NH_2$ |
| —OH | —H | —H | —H | —$CH_2NH_2$ |

-continued

| X | X' | Y | Y' | Z |
|---|---|---|---|---|
| —H | —H | —H | —H | —$C_4H_8NH_2$ |
| —H | —H | —H | —$COOCH_3$ | —COOH(Na) |
| —OH | —H | —H | —$COONHCH_3$ | —H |
| —H | —H | —H | —$COONHCH_3$ | —COOH(Na) |
| —H | —H | —H | -imidazoyl | —H |
| —H | —H | —H | -glycinyl | —H |
| —H | —H | —H | -steroidyl | —H |
| —H | —H | —H | -glycosyl | —H |
| —H | —H | —H | —H | -imidazoyl |
| —H | —H | —H | —H | -glycinyl |
| —H | —H | —H | —H | -steroidyl |
| —H | —H | —H | —H | -glycosyl |

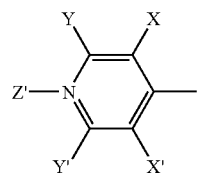

| X | X' | Y | Y' | Z' |
|---|---|---|---|---|
| —H | —H | —H | —H | —H |
| —H | —H | —H | —H | —$CH_3$ |
| —H | —H | —H | —H | —$C_6H_{12}OH$ |
| —H | —H | —H | —OH | —H |
| —H | —H | —OH | —H | —H |
| —H | —H | —H | —$COONHCH_3$ | —H |
| —H | —H | —H | —H | —benzyl |
| —H | —H | —H | —$C_6H_{12}OH$ | —$CH_3$ |
| —H | —H | —$C_6H_{13}$ | —H | —$CH_3$ |

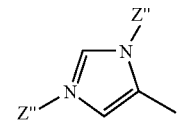

| Z'' | Z''' |
|---|---|
| —H | —H |
| —$CH_3$ | —H |
| —H | —$CH_3$ |
| —H | —$C_6H_{12}$ |
| —$C_6H_{12}$ | —H |

Figure 3:
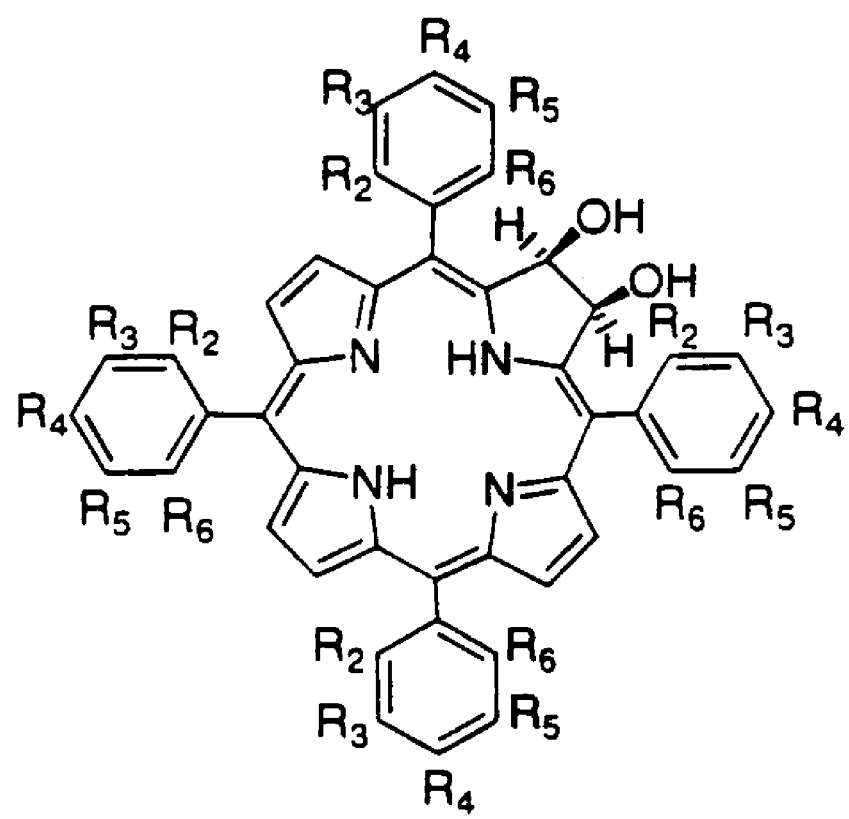
FIG. 3 shows the formula of a dihydroxychlorin of the invention, where R₂ through R₆ are independently a hydrogen atom, a lower alkyl group, a lower alkyl carboxylic acid or acid ester group, keto, hydroxy, nitro, amino, bromo, fluoro, or iodo group.

Preferred compounds of the invention include those encompassed by the formula of FIG. 3 as well as those shown in Table 1.

TABLE 1

Dihydroxychlorins

| Compound | Number | $R_2$ | $R_3$ | $R_4$ | $R_5$ | $R_6$ |
|---|---|---|---|---|---|---|
| $H_2TPC(OH)_2$ | 3 | H | H | H | H | H |
| $T(m-NO_2)PC(OH)_2$ | 4 | H | $NO_2$ | H | H | H |
| $T(p-Br)PC(OH)_2$ | 5 | H | H | Br | H | H |
| $T(m-Br)PC(OH)_2$ | 6 | H | Br | H | H | H |
| $T(m-F)PC(OH)_2$ | 7 | H | F | H | H | H |
| $T(o-F)PC(OH)_2$ | 8 | F | H | H | H | H |
| $TF_5PC(OH)_2$ | 9 | F | F | F | F | F |
| $T(p-OH)PC(OH)_2$ | 10 | H | H | OH | H | H |
| $T(m-OH)PC(OH)_2$ | 11 | H | OH | H | H | H |
| $T(p-CO_2Me)PC(OH)_2$ | 12 | H | H | $CO_2Me$ | H | H |
| $T(p-OCOEt)PC(OH)_2$ | 13 | H | H | OCOEt | H | H |
| $T(p-OCH_3)PC(OH)_2$ | 14 | H | H | $OCH_3$ | H | H |
| $T(m-OCH_3)PC(OH)_2$ | 15 | H | $OCH_3$ | H | H | H |
| $T(m,m'-OCH_3)PC(OH)_2$ | 16 | H | $OCH_3$ | H | $OCH_3$ | H |
| $T(m-OCH_3,p-OH)PC(OH)_2$ | 17 | H | $OCH_3$ | OH | H | H |
| $T(m,p,m'-OCH_3)PC(OH)_2$ | 18 | H | $OCH_3$ | $OCH_3$ | $OCH_3$ | H |
| $T(o,m,m'-OCH_3)PC(OH)_2$ | 19 | $OCH_3$ | $OCH_3$ | H | $OCH_3$ | H |
| $T(o,p,o'-OCH_3)PC(OH)_2$ | 20 | $OCH_3$ | H | $OCH_3$ | H | $OCH_3$ |
| $T(p-CH_3)PC(OH)_2$ | 21 | H | H | $CH_3$ | H | H |

TABLE 1-continued

Dihydroxychlorins

| Compound | Number | $R_2$ | $R_3$ | $R_4$ | $R_5$ | $R_6$ |
|---|---|---|---|---|---|---|
| T(o,p,o'-CH$_3$)PC(OH)$_2$ | 22 | CH$_3$ | H | CH$_3$ | H | CH$_3$ |
| T(p-SO$_3$H)PC(OH)$_2$ | 23 | H | H | SO$_3$H | H | H |
| T(p-t-Bu)PC(OH)$_2$ | 24 | H | H | t-Bu | H | H |

Additionally, meso-5-(p-bromophenyl)-10,15,20-triphenyl-2,3-dihydroxychlorin (compound 26) (mono p-Br TPC(OH)$_2$), meso-5-(p-hydroxyphenyl)-10,15,20-triphenyl-2,3-dihydroxychlorin (mono p-OH TPC(OH)$_2$) (compound 27) and meso-5-(p-nitrophenyl)-10,15,20-triphenyl-2,3-dihydroxychlorin (mono p-NO$_2$ TPC(OH)$_2$) (compound 28) were synthesized.

Figure 4:
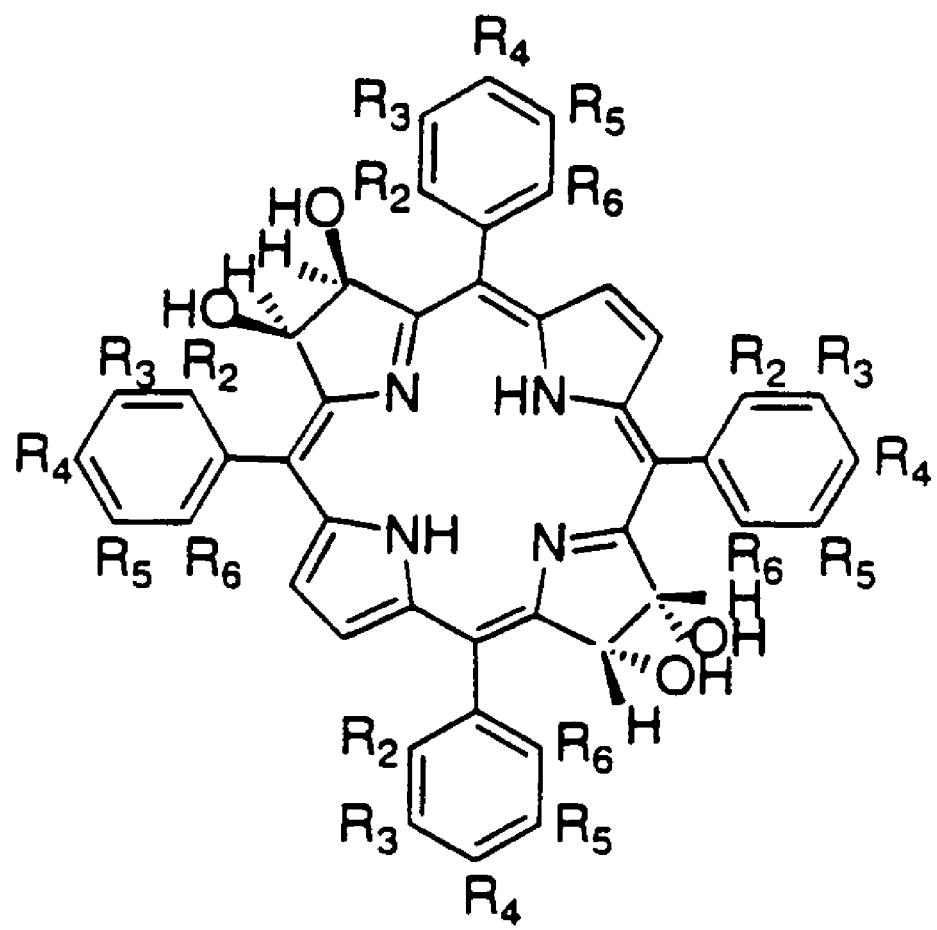
FIG. 4 shows the formula of a meso-tetraphenyl-2,3,12,13-tetrahydroxybacteriochlorin of the invention, where R₂ through R₆ are independently a hydrogen atom, a lower alkyl group, a lower alkyl carboxylic acid or acid ester group, keto, hydroxy, nitro, amino, bromo, fluoro, or iodo group.

Preferred compounds of the invention include those encompassed by the formula of FIG. 4 as well as those shown in Table 2.

Other preferred compounds include bacteriochlorins according to the structure shown in FIG. 4 and as set forth in Table 2.

TABLE 2

Tetraphenyl-2,3,12,13-tetrahydroxybacteriochlorins

| Compound | Number | $R_2$ | $R_3$ | $R_4$ | $R_5$ | $R_6$ |
|---|---|---|---|---|---|---|
| H$_2$TPB(OH)$_4$ | 29 | H | H | H | H | H |
| T(o,p,o'-OCH$_3$)PB(OH)$_4$ | 30 | OCH$_3$ | H | OCH$_3$ | H | OCH$_3$ |

The above described compounds were tested in vitro for phototoxicity and dark toxicity in L1210 cells as described in the Example section below. Twenty four compounds which were tested for cytotoxicity are listed in Table 3 below along with BPD-MA.

TABLE 3

List of LD50 values for 24 tested compounds

| Compound | Rank | LD50 (M) | Molecular Weight (g/mol) | LD50 (ng/mL) | Rank |
|---|---|---|---|---|---|
| DPC(OH)$_2$ (25) | 1 | 0.0024 | 496 | 1.2 | 1 |
| T(m,p,m'-OCH$_3$)PB(OH)$_4$ (30) | 2 | 0.0173 | 1042 | 18 | 4 |
| T(m,p,m'-OCH$_3$)PC(OH)$_2$ (18) | 3 | 0.0198 | 1008 | 20 | 5 |
| mono p-OH TPC(OH)$_2$ (27) | 4 | 0.0211 | 664 | 14 | 2 |
| T(m-OH)PC(OH)$_2$ (11) | 4 | 0.0211 | 712 | 15 | 3 |
| BPDMA (standard) | | 0.026 | 718 | 19 | |
| T(m-OCH$_3$, p-OH)PC(OH)$_2$ (17) | 5 | 0.0361 | 832 | 30 | 6 |
| T(p-CO$_2$Me)PC(OH)$_2$ (12) | 6 | 0.136 | 880 | 120 | 7 |
| H$_2$TPB(OH)$_4$ (29) | 7 | 1.03 | 682 | 700 | 8 |
| T(p-SO$_3$H)PC(OH)$_2$ (23) | 8 | 1.11 | 904 | 1000 | 9 |
| T(m-OCH$_3$)PC(OH)$_2$ (15) | 9 | 1.3 | 768 | 1000 | 9 |
| TF$_5$PC(OH)$_2$ (9) | 10 | 1.79 | 1008 | 1800 | 10 |
| T(m,m'-OCH$_3$)PC(OH)$_2$ (16) | 11 | 2.25 | 888 | 2000 | 11 |
| mono p-NO$_2$ TPC(OH)$_2$ (28) | 12 | 2.42 | 828 | 2000 | 11 |
| H$_2$TPC(OH)$_2$ (3) | 13 | 2.78 | 648 | 1800 | 10 |
| T(m-Br)PC(OH)$_2$ (6) | 14 | 4.15 | 964 | 4000 | 14 |
| T(o-F)PC(OH)$_2$ (8) | 15 | 4.17 | 720 | 3000 | 12 |
| T(p-OH)PC(OH)$_2$ (10) | 16 | 4.92 | 712 | 3500 | 13 |
| T(m-NO$_2$)PC(OH)$_2$ (4) | 17 | 5.43 | 828 | 4500 | 15 |
| T(p-Br)PC(OH)$_2$ (5) | 18 | 6.22 | 964 | 6000 | 17 |
| T(m-F)PC(OH)$_2$ (7) | 19 | 6.87 | 720 | 5000 | 16 |
| T(p-t-Bu)PC(OH)$_2$ (24) | 20 | 6.88 | 872 | 6000 | 17 |
| T(p-OCH$_3$)PC(OH)$_2$ (14) | 21 | 7.81 | 768 | 6000 | 17 |
| T(p-CH$_3$)PC(OH)$_2$ (21) | 22 | 9.94 | 704 | 7000 | 18 |
| T(o,p,o'-CH$_3$)PC(OH)$_2$ (22) | 23 | 12.3 | 816 | 10000 | 19 |

While it is standard practice to report LD50 values in terms of ng/mL, the above presentation is made since the compounds of the invention span a wide range of molecular weights. Thus, LD50 values would be more accurate when presented in units of μM. Although overall the differences in order were minimal, certain compounds, such as the trimethoxy substituted compounds (118) and (compound 30), were found to be more cytotoxic than the LD50 values presented in units of ng/mL.

The LD50 values in terms of μM also allowed the comparison of the cytotoxicity of the instant compounds with that of other photosensitizers. BPD-MA is a known photosensitizer with an LD50 value of 19 ng/mL, a molecular mass of 718 g/mol, and an LD50 of 0.026 μM which is 70 times more potent than HpD and 45 times more potent than Photofrin™ in sensitizing tumors (Richter, A. M; Waterfield, E.; Jain, A. K.; Stemberg, E. D.; Dolphin, D.; Levy, J. G. Photochem. Photobiol. 1990, 495). Five of the above compounds are more cytotoxic than BPD-MA based on the observed LD50 values. The most cytotoxic compound, diphenyl diol chlorin (125) is extremely cytotoxic: 10 times more potent than BPD-MA, 450 times more potent than Photofrin™ and 700 times more potent than HpD.

The above compounds were also tested for dark toxicity. Dark toxicity refers to the toxicity of the drug to cells in the absence of light. This toxicity is, therefore, not due to singlet oxygen mediated cellular damage. It is critical that potential photosensitizing drugs have low LD50 values in the dark so that photosensitivity after treatment is minimal, Table 4 shows that all of the compounds tested have acceptably low dark toxicity levels.

TABLE 4

List of compounds in order of decreasing dark toxicity.

| Compound | LD50dark (ng/mL) | LD20dark (ng/mL) | LD50 (ng/mL) |
|---|---|---|---|
| T(p-SO$_3$H)PC(OH)$_2$ (23) | >>20000 | >20000 | 1000 |
| T(p-OMe)PC(OH)$_2$ (14) | >20000 | 9000 | 6000 |
| T(m-OMe)PC(OH)$_2$ (13) | 20000 | 8000 | 1000 |
| T(m,p,m'-OMe)PC(OH)$_2$ (18) | 20000 | 7500 | 20 |

TABLE 4-continued

List of compounds in order of decreasing dark toxicity.

| Compound | LD50dark (ng/mL) | LD20dark (ng/mL) | LD50 (ng/mL) |
|---|---|---|---|
| $H_2$TPC(OH)$_2$ (3) | 19000 | 7000 | 1800 |
| T(o,p,o'-Me)PC(OH)$_2$ (22) | 18000 | 7500 | 10000 |
| mono p-NO$_2$ (28) | 18000 | 2000 | 2000 |
| T(m,p,m'-OMe)PB(OH)$_4$ (30) | 18000 | 1200 | 18 |
| T(o-F)PC(OH)$_2$ (8) | 15000 | 5000 | 3000 |
| T(p-OH)PC(OH)$_2$ (10) | 15000 | 5000 | 3500 |
| T(p-Me)PC(OH)$_2$ (21) | 15000 | 5000 | 7000 |
| T(m-NO$_2$)PC(OH)$_2$ (4) | 15000 | 4500 | 4500 |
| T(p-CO$_2$Me)PC(OH)$_2$ (12) | 15000 | 3000 | 120 |
| T(m-OH)PC(OH)$_2$ (11) | 12500 | 10000 | 15 |
| TF$_5$PC(OH)$_2$ (9) | 12000 | 5000 | 100 |
| T(m,m'-OMe)PC(OH)$_2$ (16) | 12000 | 5000 | 2000 |
| mono p-OH (27) | 9000 | 2000 | 14 |
| T(p-Br)PC(OH)$_2$ (5) | 8000 | 1900 | 6000 |
| $H_2$TPB(OH)$_4$ (29) | 7500 | 2500 | 700 |
| T(p-t-Bu)PC(OH)$_2$ (24) | 7000 | 2000 | 6000 |
| T(m-F)PC(OH)$_2$ (7) | 6000 | 1500 | 5000 |
| $H_2$DPC(OH)$_2$ (25) | 5000 | 1500 | 1.2 |
| T(m-OMe, p-OH)PC(OH)$_2$ (17) | 4500 | 500 | 30 |
| T(m-Br)PC(OH)$_2$ (6) | 4000 | 1500 | 4000 |

The singlet oxygen quantum yield, as exemplified by the halogenated diol chlorin compounds, appears to have only a minor influence on the observed cytotoxicity of our compounds, and therefore the difference in toxicities could be reasoned to primarily reflect the cellular uptake of the drugs. A variety of molecular properties have been proposed to be responsible for cellular uptake such as hydrophobicity, amphiphilicity, self-aggregation and the ability to bind to serum protein. An increase in lipophilicity of a photosensitizer has been found to correlate with an increase in cellular uptake of the drug due to an increase in the degree of binding to LDL (Kongshaug, M. Int. J. Biochem. 1992, 24, 1239).

Based on the above, the degree of hydrophobicity and amphiphilicity appear to be important factors in the cytotoxicity of the compounds. Whereas the porphyrin skeleton is essentially hydrophobic, the incorporation of the diol into the skeleton confers a degree of amphiphilicity to the compounds. The highly cytotoxic diphenyl diol chlorin (125) differs from tetraphenyl diol chlorin (compound 3) in that it has two fewer phenyl groups. Phenyl groups are hydrophobic, and their removal alters the degree of hydrophobicity of the molecule and at the same time increases the amphiphilicity. Additionally, the loss of the phenyl group somewhat streamlines the molecule, perhaps improving its cellular uptake. It may be surmised that the increased toxicity of the 5-(p-nitrophenyl)-10,15,20-triphenyl diol chlorin (compound 28) and the 5-(p-hydroxyphenyl)-10,15,20-triphenyl diol chlorin (compound 27) relative to their tetra-substituted analogs is due to the increased amphiphilicity and polarity that a single hydrophilic substituent would confer.

Figure 5:
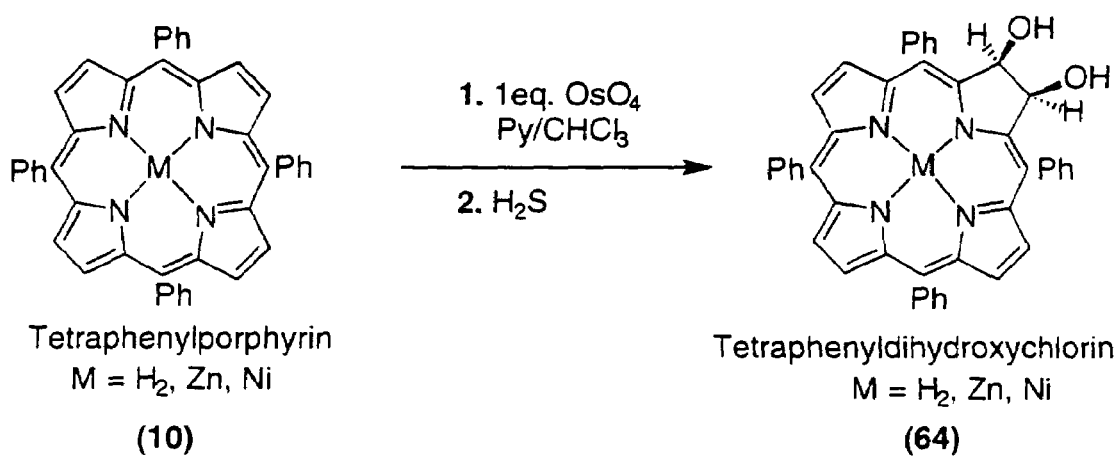
FIG. 5 shows the osmium tetroxide mediated oxidation of tetraphenylporphyrins.

General reactions to produce the above described compounds have been described in U.S. Pat. No. 5,648,485. Briefly, they may be conducted via oxidation of meso-tetraphenylporphyrin or its metallated complex occurred in a solution of chloroform or methylene chloride with a stoichiometric amount of OsO4 in the presence of pyridine. After stirring at room temperature for 5 days in the dark, reduction of the osmate complex with gaseous $H_2$S yielded the previously unknown 2,3-vic-dihydroxy-mesotetraphenylchlorin or its metallated analog in ~50% yield with ~40% starting material recovery (see FIG. 5). The resultant meso-substituted vic-diols displayed unexpected stability with dehydration and rearrangement occurring only under harsh conditions.

Figure 6:
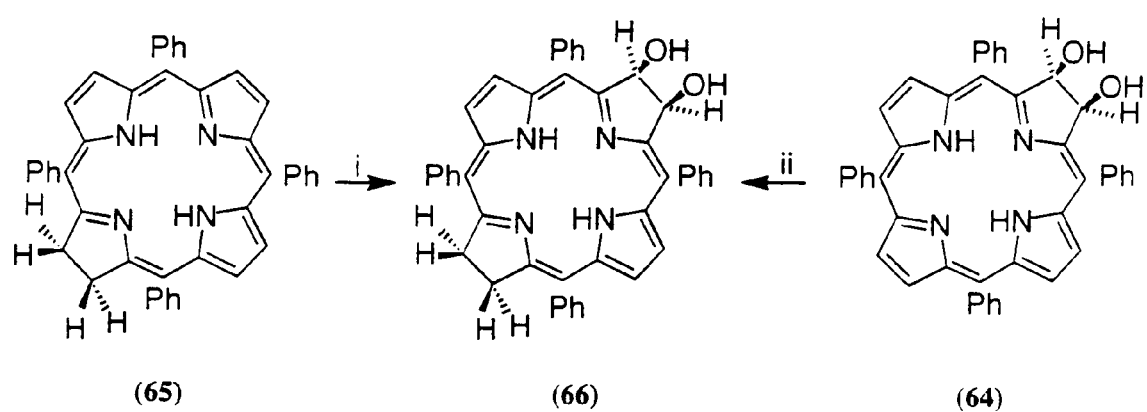
FIG. 6 shows the formation of meso-tetraphenyl-2,3-dihydroxy-12,13-dihydrobacteriochlorin (compound in the center) via a reaction of meso-tetraphenylchlorins with 1.1 eq. osmium tetroxide, pyridine, CHCl₃ and gaseous H₂S (reaction on the left) or a reaction of 2,3-vic-dihydroxy-meso-tetraphenylchlorin by reflux with pyridine, K₂CO₃, and p-toluenesulfonylhydrazine (reaction on the right).

The meso-tetraphenylchlorins and metallochlorins have also successfully been oxidized using this reaction, producing novel stable β,β'-cis-diol substituted mesotetraphenyl-2,3-dihydroxy-12,13-dihydro-bacteriochlorins and -isobacteriochlorins (see FIG. 6).

Figure 7:
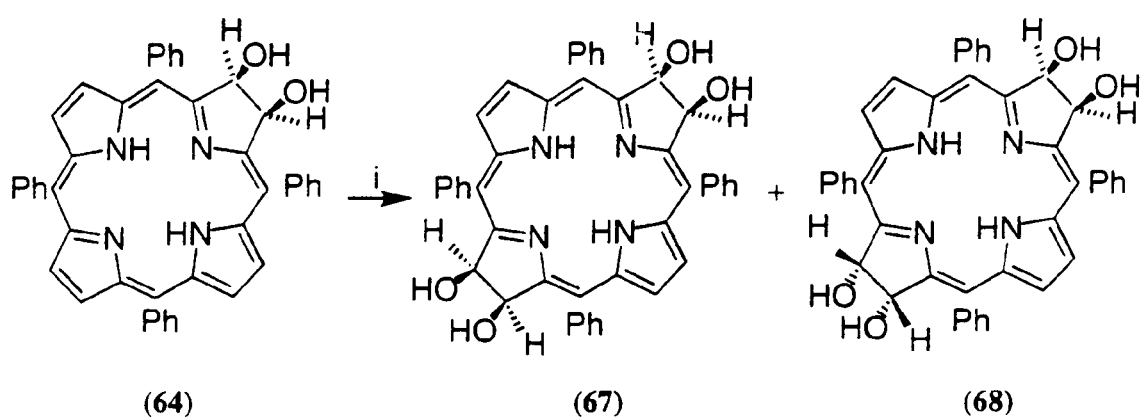
FIG. 7 shows the formation of two isomers of 2,3,12,13-bis-(vic-dihydroxy)bacteriochlorins by dihydroxylation of 2,3-vic-dihydroxy-meso-tetraphenylchlorin with one equivalent of osmium tetroxide.

Further dihydroxylation of the 2,3-vic-dihydroxy-meso-tetraphenylchlorin with one equivalent of osmium tetroxide forms two isomers of 2,3,12,13-bis-(vic-dihydroxy)bacteriochlorins in a 1:1 ratio, which are separable by chromatography (see FIG. 7).

Figure 8:
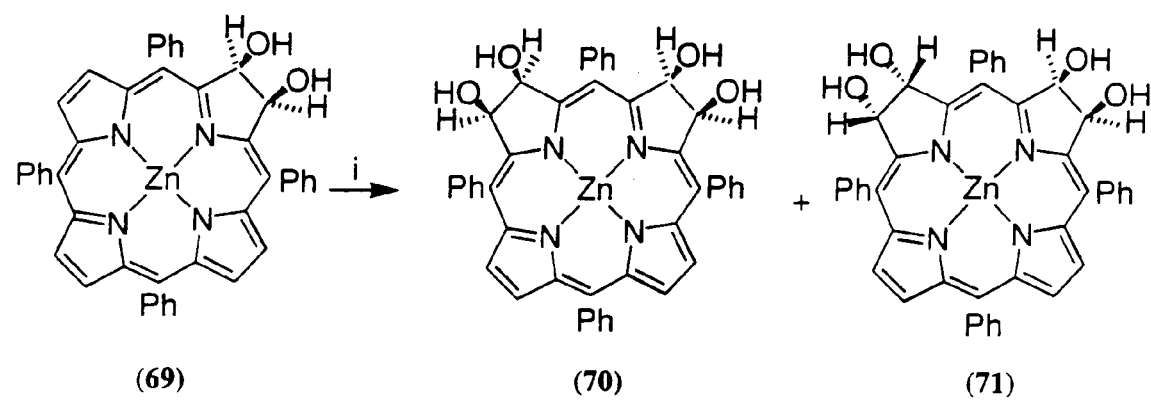
FIG. 8 shows the formation of two isomers of (meso-tetraphenyl-2,3,7,8-tetrahydroxyisobacteriochlorinato)zinc (II) from the zinc diol of 2,3-vic-dihydroxy-mesotetraphenylchlorin by reaction with one equivalent of osmium tetroxide in 2.5% pyridine/CHCl₃.

Metallation of the chlorin drastically changes the outcome of the reaction. The osmylation of 2,3-dihydroxy-meso-tetraphenylchlorin produces the two possible isomers of 2,3,12,13-tetrahydroxy-meso-tetraphenylbacteriochlorin (FIG. 7) while the osmylation of the analogous zinc diol forms the two possible isomers of 2,3,7,8-tetrahydroxy-meso-tetraphenylisobacteriochlorin (see FIG. 8). These four products can also be synthesized via treatment of their respective starting material porphyrins with two or more equivalents of osmium tetroxide. While this procedure does produce somewhat lower yields of the compounds, it is efficient in terms of being a one-pot reaction.

The osmium tetroxide reaction presents many advantages. It is a one-pot, two step synthesis with high yields and starting material recovery. Reduction of non-symmetric porphyrins generally results in the formation of all fours regioisomeric chlorins, but in this reaction only one isomer of the analogous dihydroxychlorin is formed and additional oxidation yields only two separable diastereoisomers of tetrahydroxybacteriochlorin. This allows for very high yields which is of critical economic importance. The use of tetraphenylporphyrins as starting materials has great advantages as these are the most accessible synthetic porphyrins. The number and nature of substituents on the phenyl groups can easily be varied and, therefore, the pharmacokinetics of potential pharmaceuticals can be adjusted to meet the requirements of different, specific physiological situations. Using this reaction, an entire library of compounds may be created.

Although the above osmium tetroxide based reactions are very useful and promising, there are two major drawbacks to its use for photosensitizer production on an industrial scale. First and most importantly, the osmium tetroxide reagent which is used on an equimolar scale is expensive ($50/g) and relatively toxic. Any measures to decrease the amount of osmium tetroxide required would greatly improve the chances that this reaction might be used on a large scale. Investigations into solving this disadvantage focused on possible catalytic systems and the recycling of the osmium tetroxide reagent. In order to make this reaction catalytic, the reaction time would need to be decreased. This 3–5 day reaction period is the second drawback of the osmium tetroxide oxidation of porphyrins. Efforts in this area were focused on both the reversible modification of the starting materials and also on the use of other substrates as starting materials.

Increasing the distortion of the porphyrin core is known to electronically activate the β,β' bond(s) of the molecule (Khosopour, R.; Hambright, P. J. Chem. Soc., Chem. Comm. 1972, 13). Additionally, it is known that N-alkylated porphyrins are highly distorted, with the most highly distorted porphyrins having the largest alkyl groups bound to one of the inner nitrogen atoms of the porphyrin core (Hassan, M. G. A.; Jackson, A. H.; Johnson, A. W.; Winter, M. J. Chem.

Figure 9:
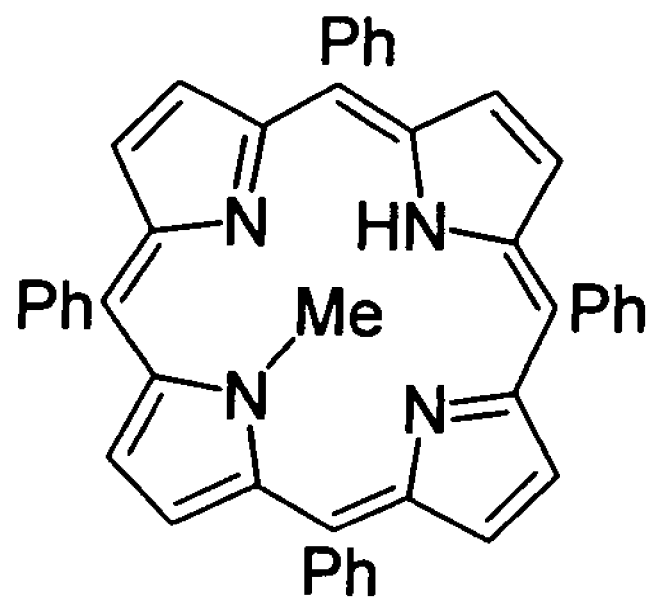
FIG. 9 shows the structure of N-methyl tetraphenylporphyrin (compound 31).

Soc., Perkin 11977, 98). We synthesized an N-alkylated porphyrin for use as a starting material in the osmium tetroxide oxidation reaction: N-methyl tetraphenylporphyrin (N-methyl TPP, compound 31, see FIG. 9). Previous studies had indicated that the osmium tetroxide mediated oxidation of N-methyl TPP appeared to be faster than unsubstituted TPP. On average, N-methyl TPP required just 6–12 hours to afford the analogous diol chlorin. Other N-alkylated tetraphenylporphyrins can also be prepared and used in the present invention.

The improved β,β'dihydroxy meso-substituted chlorin, bacteriochlorin and isobacteriochlorin compounds of the invention are useful as photosensitizers used in photodynamic therapy (PDT) and as synthetic intermediates for making related photosensitizers. Specifically, these photosensitizers are useful in sensitizing neoplastic cells or other abnormal tissues to destruction by irradiation with visible light. Upon photoactivation, the energy of photoactivation is believed to be transferred to endogenous oxygen, thus converting it to singlet oxygen. This singlet oxygen is thought by some to be responsible for the observed cytotoxic effect. Alternatively, there may be direct electron transfer from the photoactivated molecule. The method of van Lier, *Photobiological Techniques*, 216, 85–98 (Valenzo et al. eds. 1991) can be used to confirm the ability of any given compound to generate singlet oxygen effectively, thus making it a good candidate for use in photodynamic therapy. In addition, the photoactivated forms of porphyrin are able to fluoresce, and this fluorescence can aid in imaging a tumor.

Alternatively, 1,3-diphenylisobenzofuran (DPBF) may be used as a chemical quencher to determine the singlet oxygen quantum yields of various potential PDT agents (Spiller, W.; Kliesch, H.; Wohrle, D.; Hackbarth, S.; Roder, B.; Schnurpfeil, G. J. Porphyrins Phthalocyanines 1998, 2, 145). Monitoring the absorption decay of the absorption band at 415 nm (that of DPBF in DMF using UV-Visible spectrophotometry) in the presence of our compounds and during irradiation with visible light confirmed the production of singlet oxygen.

Typical indications known in the art include diagnosis and destruction of tumor tissue in solid tumors, such as those of bronchial, cervical, esophageal or colon cancer; ocular diseases characterized by unwanted neovascularization, such as age-related macular degeneration; the inhibition of secondary cataract formation in the eye (see U.S. Pat. No. 6,043, 237); the impairment of blood-borne targets such as leukemic cells and immunoreactive cells (see U.S. Pat. Nos., 5,776,966, 5,807,881 and 5,868,695); the removal of unwanted microorganisms; dissolution of plaques in blood vessels (see, e.g., U.S. Pat. No. 4,512,672, which is hereby incorporated by reference); treatment of topical conditions such as acne, athlete's foot, warts, papilloma and psoriasis; treatment of biological products, such as blood for transfusion to eliminate infectious agents; and the prevention of transplant rejection by pre-treating the graft tissue.

Additionally, when metals such as In or Tc are used, the metallated pigment compounds of the invention have diagnostic use in nuclear medicine. Similarly, when M is Mn(III) or Gd(III), the compounds may be useful in magnetic resonance imaging. These are also applications where, due the variability possible with respect to the substitution patterns, significantly improved biodistribution properties may be achieved by using the compounds of the invention.

The photosensitizers made from the compounds of the invention can be formulated into pharmaceutical compositions for administration to the subject or applied to an in vitro target using techniques generally known in the art. Additionally, formulations as liposomal compositions has also been demonstrated (copending U.S. patent application Ser. No. 08/489,850). A summary of such pharmaceutical compositions may be found, for example, in Remington's Pharmaceutical Sciences, Mack Publishing Co., Easton, Pa. The compounds of the invention can be used singly or as components of mixtures.

Generally, for the diagnosis or treatment of solid tumors, the compound of the invention, labeled or unlabeled, is administered systemically, such as by injection. Injection may be intravenous, subcutaneous, intramuscular, or even intraperitoneal. Injectables can be prepared in conventional forms, either as liquid solutions or suspensions, solid forms suitable for solution or suspension in a liquid prior to injection, or as emulsions. Suitable excipients are, for example, water, saline, dextrose, glycerol and the like. Of course, these compositions may also contain minor amounts of nontoxic, auxiliary substances, such as wetting or emulsifying agents, pH buffering agents, and so forth.

Systemic administration can be implemented through implantation of a slow release or sustained release system, by suppository, or, if properly formulated, orally. Formulations for these modes of administration are well known in the art, and a summary of such methods may be found, for example, in Remington's Pharmaceutical Sciences (supra).

If treatment is to be localized, such as for the treatment of superficial tumors or skin disorders, the compound can be administered topically using standard topical compositions, such as lotions, suspensions, or pastes.

The quantity of the photosensitizer compound to be administered depends upon the choice of active ingredient, the condition to be treated, the mode of administration, the individual subject, and the judgment of the practitioner. Depending on the specificity of the preparation, smaller or larger doses may be needed. For compositions that are highly specific to target tissues, such as those with a highly specific monoclonal immunoglobulin preparation or a specific receptor ligand, dosages in the range of 0.05–1 mg/kg are suggested. For compositions that are less specific to the target tissue, larger doses, up to 1–10 mg/kg may be needed. The foregoing ranges are merely suggestive, as the number of variables in regard to an individual treatment regime is large, and considerable excursions from these recommended values are not uncommon.

In addition to in vivo use, the compounds made from the intermediate compounds of the invention can be used in the treatment of materials in vitro to destroy harmful viruses or other infectious agents. For example, blood plasma or blood that is to be used for transfusion or banked for future transfusion, can be treated with the compounds of the invention and irradiated to effect sterilization. In addition, biological products such as Factor VIII, which are prepared from biological fluids, can be irradiated in the presence of the compounds of the invention to destroy contaminants.

The invention will be further clarified by the following examples, which are intended to be purely illustrative of the invention.

EXAMPLE 1

Biological Testing

The tested compounds (see Tables 1–4 above) were dissolved in DMSO with the exception of $T(p-SO_3H)PC(OH)_2$ (123) which was dissolved in water. The solubility of the compounds was tested by placing the drug (1 mg) in 1 mL of DMSO and then spinning at 10000 rpm for 10 minutes and checking for pellet formation. The concentration of the compounds that formed a pellet was decreased from 1 mg/mL to 0.5 mg/mL DMSO and retested to show an absence of pellet.

Phototoxicity was determined with L11210 cells in the presence of the compound as follows: the L1210 cells were exposed to varying concentrations of the compounds in 96-well microtiter plates for one hour at 37° C. and 5% $CO_2$. No fetal calf serum (FCS) was added at this time. The plate was then illuminated for one hour after which a 10% aqueous FCS solution was added to the wells. The plates were then returned to the $CO_2$ incubator overnight. After incubation, the cells were assayed for viability using the MTT assay (Mossman, T. J. Immunol. Meth. 1983, 65, 55).

Dark cytotoxicity was determined while the plates were wrapped in aluminum foil while under the light source.

EXAMPLE 2

General Chlorin Synthesis

Tetraphenylporphyrin (1 g, 1.63 mmol) was dissolved in a solution of 210% pyridine in reagent grade chloroform. The volume of solvent used was the minimum amount required to dissolve the particular porphyrin being used and ranged from 0.25 to 1 mL/mg. Osmium tetraoxide (450 mg, 1.1 eq) was added to the solution and reaction stirred at room temperature in the dark. The reaction progress was monitored by TLC or UV-Visible spectroscopy until no further reaction was observed (35 days). The reaction was then purged with hydrogen sulfide gas for 10 minutes, and then purged with air until the solvent had evaporated. The solid was then dissolved in a 10% MeOH:$CHCl_3$ solution and filtered. The filtrate was evaporated to dryness and chromatographed (silica, 5% MeOH:$CHCl_3$) to yield the analogous diol chlorin in 40–60% yield.

EXAMPLE 3

Preparation of compound N-Methyl-5,10,15–20-tetraphenylporphyrin (compound 31); see Khosopour, R.; Hambright, P. J. Chem. Soc., Chem. Comm. 1972, 13

Tetraphenylporphyrin (50 mg, 0.08 mmol) was dissolved in glacial acetic acid (5 mL), and m-xylene (85 mL). Methyl iodide (10 mL) was added to the solution. The mixture was refluxed for 30 hours after which the solvent was removed in vacuo. The remaining solids were dissolved in benzene (25 mL) and dimethylsulfate (0.5 mL) was added. The mixture was refluxed for 45 minutes, cooled to room temperature and neutralized with solid sodium carbonate. The reaction was filtered, and the solvent evaporated to dryness. Column chromatography (acidic alumina; 5% MeOH:$CH_2Cl_2$) gave (131) in 5% yield.

EXAMPLE 4

Characterization of Compounds

The infrared spectra were measured with a Perkins-Elmer Model 834 FT-IR instrument. The $^1$H-NMR were measured on a Bruker AC-200 spectrometer (200 MHz) or a Bruker WH-400 (400 MHz). $^{13}$C-NMR were measured on a Varian XL-300 (75 MHz) spectrometer. The NMR are expressed on the scale and are referenced to residual solvent peaks and TMS. The low and high resolution FAB and EI mass spectra were obtained on a AEI MS902 and a Kratos MS50. The UV-Visible spectra were measured on a Hewlett-Packard HP 8452A photodiode array spectrophotometer and the data were processed on a microcomputer (CA Kricket Graph III software). Elemental analyses were performed on a Fisons CHN/O Analyzer, Model 1108. Chromatography was performed on silica gel 60, 70–230 mesh, supplied by E. Merck Co. Preparative thin layer chromatography was prepared on pre-coated 10 cm×10 cm, 0.5 mm thick Merck silica gel plates.

EXAMPLE 5

Spectral Data of Select Compounds $H_2TPC(OH)_2$ (compound 3) (see Bruckner, C.; Dolphin, D. Tetrahedron Lett. 1995, 36, 9425) Rf 0.7(Silica-$CH_2Cl_2$); UV-Vis ($CH_2Cl_2$) max 416, 520, 546, 594, 644 nm; $^1$H-NMR (200 MHz, $CDCl_3$)=−1.80 (br s, 2H), 3.12 (s, 2H), 6.36 (s, 2H), 7.72–7.82 (m, 12H), 7.80 (d, 2H), 8.10 (s, 4H), 8.15 (d, 2H), 8.35 (d, 2H), 8.44 (s, 2H), 8.64 (d, 2H), MS (EI, 320° C.) m/e 648 (M+, 100%).

T(m-$NO_2$)PC(OH)$_2$ (compound 4) $R_f$ 0.76 (Silica-2% MeOH:$CHCl_3$); UV-V is ($CH_2Cl_2$) max 412, 518, 548, 548, 594, 644 mm; $^1$H-NMR (200 MHz, $CDCl_3$)=−1.80 (br s, 2H), 6.78 (d, 2H, Hp), 7.42 (t, 2H, Hm), 7.67 (br m, 2H, Ho), 7.86 (2d, 2H,Ho), 7.95 (m, 4H, Hm and Hp), 8.14 (d, 2H, Ho), 8.27 (br m, 2H, Ho), 8.38 (d, 2H, H), 8.48 (s, 2H, H), 8.58 (d, 2H, H); MS (EI, 320° C.) m/e 828 (M+, 30%), 810 (M+—$H_2O$, 100%). T(p-Br)PC(OH)$_2$ (compound 5) Rf 0.65 (Silica-2% MeOH:$CHCl_3$); UV-Vis ($CH_2Cl_2$) max 412, 486 (sh), 516, 544, 592, 648 nm; $^1$H-NMR (200 MHz, $CDCl_3$) =−1.80 (br s, 2H), 8.0 (br s, 2H, Ho), 8.2 (br s, 6H, Ho), 8.3 (d, J=4.76 Hz, 2H, H), 8.4 (d, J=7.55 Hz, 8H, Hm), 8.45 (s, 2H, H), 8.60 (d, J=4.72 Hz, H); MS (EI, 320° C.) m/e 964 (M+, 10%), 946 (M+—$H_2O$, 100%).

T(m-Br)PC(OH)$_2$ (compound 6) Rf 0.74 (Silica-2% MeOH:$CHCl_3$); UV-Vis ($CH_2Cl_2$) max 418, 514, 548, 586, 644 nm; $^1$H-NMR (400 MHz, $CDCl_3$)=−1.85 (br s, 2H), 6.88 (d, 2H, Hp), 7.39 (t, 2H, Hm), 7.57 (br m, 2H, Ho), 7.74 (2d, 2H, Ho), 7.83 (m, 4H, Hm and Hp), 8.04 (d, 2H, Ho), 8.07 (br m, 2H, Ho), 8.32 (d, 2H, H), 8.46 (s, 2H, H), 8.63 (d, 2H, H); MS (EI, 320° C.) m/e 964 (M+, 15%), 946 (M+—$H_2O$, 100%).

T(m-F)PC(OH)$_2$ (compound 7) Rf 0.64 (Silica-2% MeOH:$CHCl_3$); UV-Vis ($CH_2Cl_2$) max 414, 518, 542, 596, 650 nm; $^1$H-NMR (200 MHz, $CDCl_3$)=6.28 (s, 2H), 7.0 (dd, 2H), 7.2 (d, 2H), 7.3 (br m, 2H), 7.4–7.6 (m, 12H), 8.4 (s, 2H), 8.6 (d, 2H); MS (EI, 320° C.) m/e 720 (M+, 100%), 704 (M+-0, 30%).

T(o-F)PC(OH)$_2$ (compound 8) Rf 0.62 (Silica-2% MeOH:$CHCl_3$); UV-Vis ($CH_2Cl_2$) max 416, 518, 544, 592, 648 nm; $^1$H-NMR (400 MHz, $CDCl_3$)=−1.80 (brs, 2H), 6.30 (s, 2H), 7.46 (m, 6H, Hm and Hp), 7.70 (m, 6H, Hm and Hp), 8.05 (m, 2H, Ho), 8.30 (d, 2H, Ho), 8.35 (d, J=4.70 Hz, 2H, H), 8.45 (s, 2H, H), 8.62 (d, J=4.31 Hz, 2H, H); MS (EI, 320° C.) m/e 702 (M+—$H_2O$, 60%).

TF5PC(OH)$_2$ (compound 9) Rf 0.60 (Silica-$CH_2Cl_2$); UV-Vis ($CH_2Cl_2$) max 410, 506, 596, 650 nm; $^1$H-NMR (200 MHz, $CDCl_3$)=−1.72 (s, 2H), 6.0 (s, 2H), 8.19 (d, 2H, H), 8.39 (d,2H, H); MS (EI, 320° C.) m/e 1008 (M+, 10%), 990 (M+—$H_2O$, 20%); 974 (M+-2 HO, 100%).

T(p-OH)PC(OH)$_2$ (compound 10) Rf 0.52 (Silica-2% MeOH:$CHCl_3$); UV-Vis ($CH_2Cl_2$) max 422, 520, 558, 596, 652 nm; $^1$H-NMR (200 MHz, $CDCl_3$)=−1.8 (br s, 2H), 6.3 (s, 2H), 7.3 (m, 8H), 7.8 (d, 2H), 8.0 (br m, 2H), 8.2 (m, 4H), 8.3 (d, 2H), 8.5 (s, 2H), 8.7 (d, 2H); MS (EI, 320° C.) m/e 712 (M+, 15%), 694 (M+—$H_2O$, 60%).

T(m-OH)PC(OH)$_2$ (compound 11) Rf 0.52(Silica-$CH_2Cl_2$);UV-Vis ($CH_2Cl_2$) max 416, 514, 548, 592, 646 nm; $^1$H-NMR (200 MHz, $CDCl_3$)=5.17 (br s, 2H), 6.18 (s, 2H), 7.07 (dd, 2H), 7.18 (dd, 2H), 7.30 (m, 2H), 7.39–7.58 (m, 10H), 8.36 (br s, 2H), 8.43 (s, 2H), 8.69 (d, 2H), 9.75 (br s, 4H); MS (EI, 320° C.) m/e 712 (M+, 5%), 694 (M+—$H_2O$, 100%).

T(p-$CO_2$Me)PC(OH)$_2$ (compound 12) Rf 0.71 (Silica-2% MeOH:$CHCl_3$); UV-Vis ($CH_2Cl_2$) max 422, 518, 558, 600, 646 nm; $^1$H-NMR (200 MHz, $CDCl_3$)=−1.80 (br s, 2H), 8.0 (br s, 2H, Ho), 8.2 (br s, 6H, Ho), 8.28 (d, J=4.76 Hz, 2H, H), 8.38 (d, J=7.55 Hz, 8H, Hm), 8.43 (s, 2H), 8.59 (d, J=4.72 Hz, H); MS (EI, 320° C.) m/e 880 (M+, 65%), 862 (M+—$H_2O$, 100%).

T(p-OCOEt)PC(OH)$_2$ (compound 13) Rf 0.66 (Silica-$CH_2Cl_2$); UV-Vis ($CH_2Cl_2$) max 416, 514, 548, 592, 644 nm; $^1$H-NMR (200 MHz, $CDCl_3$)=7.30 (br s, 2H, Ho), 7.5 (br s, 6H, Ho), 8.0 (m, 8H, Hm), 8.2 (d, 2H), 8.4 (s, 2H, H), 8.55 (d, H).

T(p-OMe)PC(OH)$_2$ (compound 14) Rf 0.67 (Silica-2% MeOH:$CHCl_3$); UV-Vis ($CH_2Cl_2$) max 420, 520, 556, 596, 648 nm; $^1$H-NMR (400 MHz, $CDCl_3$)=−1.8 (br s, 2H), 4.1 (2s, 12H), 6.4 (s, 2H), 7.3 (m, 12H), 7.7 (d, 2H), 8.1 (m, 6H), 8.3 (d, 2H), 8.5 (s, 2H), 8.7 (d, 2H); MS (EI, 320° C.) m/e 814 (ZnM+—$H_2O$, 15%).

T(m-OMe)PC(OH)$_2$ (compound 15) Rf 0.6 (Silica-$CH_2Cl_2$); UV-Vis ($CH_2Cl_2$) max 416, 516, 546, 584, 646 nm; $^1$H-NMR (200 MHz, $CDCl_3$)=4.0 (2s, 12H), 6.28 (s, 2H), 7.0 (d, 2H), 7.1 (d, 2H), 7.30 (m, 2H), 7.5 (m, 4H), 8.3 (d, 2H), 8.4 (s, 2H), 8.5 (d, 2H); MS (EI, 320° C.) m/e 768 (M+, 10%), 750 (M+—$H_2O$, 100%).

T(m,m'-OMe)PC(OH)$_2$ (compound 16) Rf 0.43 (Silica-$CH_2Cl_2$); UV-Vis ($CH_2Cl_2$) max 416, 520, 548, 592, 646 nm; $^1$H-NMR (400 MHz, $CDCl_3$)=−1.85 (s, 2H), 3.9 (m, 12H), 6.4 (s, 2H), 6.8 (s, 2H), 6.85 (s, 2H), 7.1 (s, 2H), 7.25 (s, 2H), 7.3 (s, 2H), 7.4 (s, 2H), 8.4 (d, 2H), 8.6 (s, 2H), 8.75 (d, 2H).

T(m-OMe, p-OH)PC(OH)$_2$ (compound 17) Rf 0.50 (Silica-$CH_2Cl_2$); UV-Vis ($CH_2Cl_2$) max 418, 484 (sh), 518, 544, 596, 646 nm; $^1$H-NMR (200 MHz, $CDCl_3$)=1.95 (s, 2H), 3.88 (s, 12H), 5.96 (s, 2H), 7.25 (d, 4H), 7.68 (d, 8H), 8.94 (s, 8H); MS (EI, 320° C.) m/e 832 (M+, 10%), 814 (M+—$H_2O$, 100%).

T(m,p,m'-OMe)PC(OH)2 (compound 18) Rf 0.65 (Silica-$CH_2Cl_2$); UV-Vis ($CH_2Cl_2$) max 418, 518, 548, 592, 644 nm; $^1$H-NMR (400 MHz, $CDCl_3$)=−1.98 (s, 2H), 3.81(s, 3H), 3.86 (s, 3H), 3.88 (s, 3H), 3.90 (s, 3H), 3.92 (s, 3H), 3.95 (s, 3H), 5.30 (d, 2H), 6.39 (d, 2H), 7.15 (s, 2H), 7.35 (s, 2H), 7.41(s, 2H), 7.43 (s, 2H), 8.46 (d, 2H), 8.59 (d, 2H), 8.77 (d, 2H); MS (EI, 320° C.) m/e 1008 (M+, 30%), 990 (M+—$H_2O$, 100%).

T(o,m,m'-OMe)PC(OH)$_2$ (compound 19) Rf 0.60 (Silica-$CH_2Cl_2$); UV-Vis ($CH_2Cl_2$) max 418, 518, 548, 592, 644 nm; $^1$H-NMR (200 MHz, $CDCl_3$)=−1.8 (br s, 2H), 4.15 (m, 36H), 6.05 (s, 2H), 6.8 (m, 4H), 7.5 (m, 4H), 8.2 (d, 2H), 8.4 (s, 2H), 8.6 (d, 2H); MS (EI, 320° C.) m/e 1008 (M+, 15%), 990 (M+—$H_2O$, 100%).

T(o,p,o'-OMe)PC(OH)$_2$ (compound 20) Rf 0.70 (Silica-$CH_2Cl_2$); UV-Vis ($CH_2Cl_2$) max 418, 518, 544, 594, 646 nm; $^1$H-NMR (200 MHz, $CDCl_3$)=−1.7 (br s, 2H), 4.0 (m, 36H), 6.05 (s, 2H), 6.5 (m, 8H), 8.2 (d, 2H), 8.4 (s, 2H), 8.6 (d, 2H); MS (EI, 320° C.) m/e 1008 (M+, 10%), 990 (M+—$H_2O$, 100%).

T(p-Me)PC(OH)$_2$ (compound 21) Rf 0.90 (Silica-5% MeOH:$CHCl_3$);UV-Vis ($CH_2Cl_2$) max 416, 520, 546, 594, 644 nm; $^1$H-NMR (200 MHz, $CDCl_3$)=−1.78 (br s, 2H), 2.45 (2s, 12H, Me), 6.30 (s, 2H), 7.2 (m, 8H, Hm), 7.7 (m, 4H, Ho), 8.0 (m, 4H, Ho), 8.30 (d, 2H, H), 8.40 (s, 2H, H), 8.56 (d, 2H, H); MS (EI, 320° C.) m/e 704 (M+, 5%), 686 (M+—$H_2O$, 10%), 670 (M+, 100%).

T(o,p,o'-Me)PC(OH)$_2$ (compound 22) Rf 0.94 (Silica-5% MeOH:$CHCl_3$); UV-Vis ($CH_2Cl_2$) max 418, 480 (sh), 516, 542, 592, 646 nm; $^1$H-NMR (200 MHz, $CDCl_3$)=1.78 (br s, 2H), 6.0 (s, 2H), 7.25 (m, 8H, Hm), 8.15 (d, 2H, H), 8.28 (s, 2H, H), 8.45 (d, 2H, H); MS (EI, 320° C.) m/e 816 (M+, 30%), 798 (M+—$H_2O$, 100%).

T(p-$SO_3$H)PC(OH)$_2$ (compound 23) Rf 0.1 (Silica-$CH_2Cl_2$); UV-Vis ($CH_2Cl_2$) max 420, 520, 548, 592, 648 nm.

T(p-t-Bu)PC(OH)$_2$ (compound 24) Rf 0.75 (Silica-$CH_2Cl_2$); UV-Vis ($CH_2Cl_2$) max 418, 522, 548, 594, 644 nm; $^1$H-NMR (200 MHz, $CDCl_3$)=3.45 (2s, 36H, Me), 6.2 (s, 2H), 7.0 (m, 8H, Hm), 7.5 (m, 4H, Ho), 7.8 (m, 2H, Ho), 8.0 (br m, 2H, Ho), 8.3 (d, 2H, H), 8.4 (s, 2H, H), 8.6 (d, 2H, H); MS (EI, 320° C.) m/e 935 (M+, 10%), 916 (M+—$H_2O$, 60%).

$H_2$DPC(OH)$_2$ (compound 25) Rf 0.3 (Silica-$CH_2Cl_2$); UV-Vis ($CH_2Cl_2$) max 402, 504, 530, 584, 638 nm; $^1$H-NMR (200 MHz, $CDCl_3$)=−2.1 (br s, 1H), −1.9 (br s, 1H), 6.05 (d, J=6.3 Hz, 1H), 6.35 (d, J=6.4 Hz, 1H), 7.65 (m, 6H), 7.9 (d, 1H), 8.10 (d, J=4.4 Hz, 2H), 8.25 (d, 1H), 8.45 (d, J=4.5 Hz, 1H), 8.65 (d, J=4.5 Hz, 1H), 8.80 (d, J=4.5 Hz, 1H), 8.95 (d, J=4.5 Hz, 1H), 9.0 (d, J=4.4 Hz, 1H), 9.15 (d, J=4.3 Hz, 1H), 9.90 (s, 1H), 9.34 (s, 1H); MS (EI) m/e calc'd for $C_{32}H_{24}N_4O_2Ni$: 496.18945, found 496.18923 (M+, 100%).

mono p-Br PC(OH)$_2$ (compound 26) Rf 0.4 (Silica-$CH_2Cl_2$); UV-Vis ($CH_2Cl_2$) max 412, 508, 528, 596, 644 nm; $^1$H-NMR (200 MHz,$CDCl_3$)=6.2 (d, 2H), 7.0 (d, 2H), 7.5 (m, 12H), 7.8 (2d, 1H), 8.0 (m, 4H), 8.2 (d, 1H), 8.3 (d, 1H), 8.35 (s, 2H), 8.5 (d, 1H); MS (EI, 320° C.) m/e 726 (M+, 20%), 709 (M+—$H_2O$, 100%).

mono p-OH PC(OH)$_2$ (compound 27) Rf 0.2 (Silica-$CH_2Cl_2$); UV-Vis ($CH_2Cl_2$) max 412, 520, 548, 594, 644 nm; $^1$H-NMR (200 MHz,$CDCl_3$)=6.4 (d, 2H), 7.1 (d, 2H), 7.5 (m, 12H), 7.85 (2d, 1H), 8.0 (m, 4H), 8.1 (d, 1H), 8.25 (d, 1H), 8.35 (s, 2H), 8.7 (d, 1H); MS (EI, 320° C.) m/e 662 (M+, 5%), 990 (M+—$H_2O$, 646%).

mono p-$NO_2$ PC(OH)$_2$ (compound 28) Rf 0.4 (Silica-$CH_2Cl_2$); UV-Vis ($CH_2Cl_2$) max 418, 516, 546, 596, 646 nm; $^1$H-NMR (200 MHz,$CDCl_3$)=7.2 (d, 2H), 7.65 (m, 12H), 7.8 (d, 2H), 8.10 (m, 4H), 8.2 (d, 1H), 8.3 (s, 2H), 8.4 (d, 1H).

N-Methyl-5,10,15–20-tetraphenylporphyrin (compound 31);

RF 0.1 (silica −5% MeOH:$CH_2Cl_2$); $^1$H-NMR (200 MHz, $CDCl_3$)=−4.0 (br s, 1H), 7.42 (s, 2H), 7.70–7.85 (m, 12H), 8.15–8.40 (m, 8H), 8.46 (d, 2H), 8.64 (d, 2H), 8.82 (s, 2H), 8.4 (d, 2H). UV-Vis ($CH_2Cl_2$) max 440, 532, 578, 618, 670 nm; MS (LSIMS) m/e 629 (M+, 100%).

What is claimed is:

1. A compound having the formula:

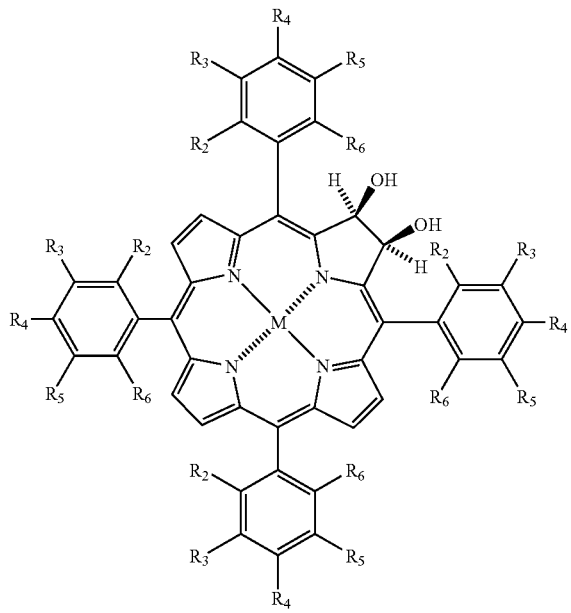

or

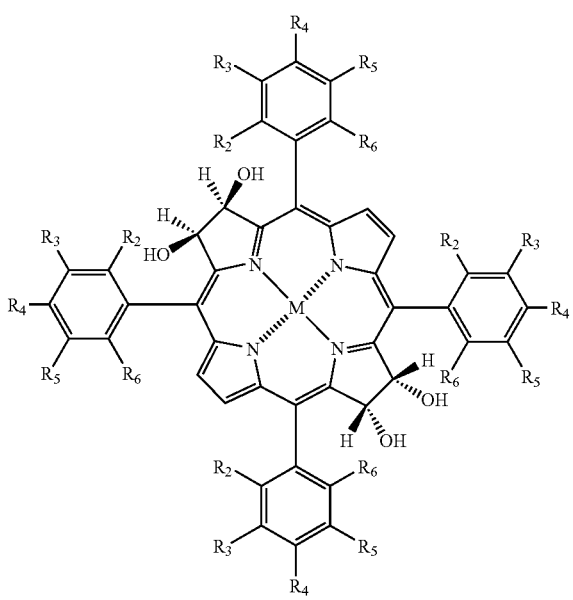

wherein each $R_2$, $R_3$, $R_4$, $R_5$ and $R_6$ are independently H, nitro, halo, hydroxy, alkoxy, $CO_2R$ or OCOR, wherein each R is $C_{1-6}$ alkyl;

M is a metal selected from the group consisting of Ni(II), Cu(II), Zn, Sn, Ge, Si, Ga, Al, Mn(III), Gd(III), In and Tc or 2H atoms;

and wherein said compound is selected from the group consisting of T(m-$NO_2$)PC(OH)$_2$ (compound 4), T(p-Br)PC(OH)$_2$ (compound 5), T(m-Br)PC(OH)$_2$ (compound 6), T(m-F)PC(OH)$_2$ (compound 7), T(o-F)PC(OH)$_2$ (compound 8), TF$_5$PC(OH)$_2$ (compound 9), T(m-OH)PC(OH)$_2$ (compound 11), T(p-CO$_2$Me)PC(OH)$_2$ (compound 12), T(p-OCOEt)PC(OH)$_2$ (compound 13), T(p-OCH$_3$)PC(OH)$_2$ (compound 14), T(m-OCH$_3$)PC(OH)$_2$ (compound 15), T(m,m'—OCH$_3$)PC(OH)$_2$ (compound 16), T(m-OCH$_3$,p-OH)PC(OH)$_2$ (compound 17), T(o,m,m'—OCH$_3$)PC(OH)$_2$ (compound 19), T(o,p,o'—OCH$_3$)PC(OH)$_2$ (compound 20), T(p-CH$_3$)PC(OH)$_2$ (compound 21), T(o,p,o'—CH$_3$)PC(OH)$_2$ (compound 22), and T(o,p,o'—OCH$_3$)PB(OH)$_4$ (compound 30), wherein each T is independently tetra.

2. The compound of claim 1, where M is Zn.

3. The compound of claim 1, where M is 2H atoms.

4. The compound of claim 1, selected from the group consisting of T(m-OH)PC(OH)$_2$ (compound 11) and T(o,p,o'—OCH$_3$)PB(OH)$_4$ (compound 30).

5. A β,β-dihydroxy meso-substituted chlorin compound selected from the group consisting of diphenyl-2,3-dihydroxychlorin (compound 25), meso-5-(p-bromophenyl)-10,15,20-triphenyl-2,3-dihydroxychlorin (compound 26), meso-5-(p-hydroxyphenyl)-10,15–20-triphenyl-2,3-dihydroxychlorin (compound 27), and meso-5-(p-nitrophenyl)-10,15,20-triphenyl-2,3-dihydroxychlorin (compound 28).

6. The compound of claim 5, wherein said compound is complexed with a metal selected from the group consisting of Ni(II), Cu(II), Zn, Sn, Ge, Si, Ga, Al, Mn(III), Gd(III), In and Tc.

7. The compound of claim 6, where said metal is Zn.

* * * * *